US009662312B2

(12) United States Patent
Zhang et al.

(10) Patent No.: US 9,662,312 B2
(45) Date of Patent: May 30, 2017

(54) METHOD FOR TREATING GLOMERULOSCLEROSIS

(71) Applicant: Ligand Pharmaceuticals Inc., San Diego, CA (US)

(72) Inventors: Jinkun Zhang, San Diego, CA (US); Zofia E. Dziewanowska, La Jolla, CA (US); Rene Belder, Hopewell, NJ (US); Ian Henderson, San Diego, CA (US); Joseph B. Bogardus, Keene, NY (US); Zhaoying Zhang, Monmouth Junction, NJ (US)

(73) Assignee: Ligand Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 14/631,768

(22) Filed: Feb. 25, 2015

(65) Prior Publication Data
US 2015/0164865 A1 Jun. 18, 2015

Related U.S. Application Data

(63) Continuation of application No. 13/720,452, filed on Dec. 19, 2012, now abandoned, which is a continuation of application No. 13/471,364, filed on May 14, 2012, now abandoned, which is a continuation of application No. 13/262,223, filed as application No. PCT/US2010/029093 on Mar. 29, 2010, now abandoned.

(60) Provisional application No. 61/165,419, filed on Mar. 31, 2009, provisional application No. 61/165,447, filed on Mar. 31, 2009.

(51) Int. Cl.
C07D 413/12 (2006.01)
A61K 31/422 (2006.01)
A61K 9/20 (2006.01)

(52) U.S. Cl.
CPC ......... *A61K 31/422* (2013.01); *A61K 9/2013* (2013.01); *A61K 9/2018* (2013.01); *A61K 9/2031* (2013.01); *A61K 9/2054* (2013.01); *A61K 9/2059* (2013.01); *C07D 413/12* (2013.01)

(58) Field of Classification Search
None
See application file for complete search history.

(56) References Cited

U.S. PATENT DOCUMENTS

| 6,638,937 | B2 | 10/2003 | Murugesan et al. |
| 6,835,741 | B2 | 12/2004 | Murugesan et al. |
| 2002/0143024 | A1 | 10/2002 | Murugesan et al. |
| 2004/0106833 | A1 | 6/2004 | San et al. |

FOREIGN PATENT DOCUMENTS

| CN | 1308536 A | 8/2001 |
| JP | 2003-520785 A | 7/2003 |
| JP | 2003-520785 T | 2/2008 |
| WO | 00/01389 A1 | 1/2000 |
| WO | 01/44239 A2 | 6/2001 |

OTHER PUBLICATIONS

Murugesan et al., "Dual Angiotensin II and Endothelin A Receptor Antagonists: Synthesis of 2'-Substituted N-3-Isoxazolyl Biphenylsulfonamides with Improved Potency and Pharmacokinetics," *J. Med. Chem.* 48:171-179, 2005.
Neutel et al., "Abstract 4420: Results of a Double Blind Placebo Controlled Study to Evaluate the Efficacy and Safety of PS433540 in Human Subjects with Hypertension," *Circulation* 118(S_886), 2008, 1 page.
Neutel et al., "Results of a Double Blind, Placebo Controlled Study to Evaluating PS433540, a Novel Dual Acting Receptor Antagonist in Stage I and II Hypertenives," *J. Am. Soc. Nephrol.* 19 2008, 2 pages.
O'Riordan, "Dual-acting receptor antagonist reduces systolic blood pressure: No safety signals raised in phase 2a trial," *Heartwire*, May 16, 2008, retrieved from http://www.theheart.org/article/867339.do, on Jun. 8, 2013, 3 pages.
Pharmacopeia, "Investor Presentation PS433540 Phase 2a Study Results," May 16, 2008, retrieved from http://www.sec.gov/Archives/edgar/data/1273013/000110465908033876/a08-14253 2ex99d2.htm, 12 pages.
Thompson Pharma Integrity, Entry 307300 for Drug Name "PS433540," Retrieved Jun. 8, 2013, 2 pages.
Chinese Office Action dispatched Oct. 27, 2015, for corresponding CN Application No. 201410045095.9, with English Translation, 10 pages.
Communication pursuant to Article 94(3) EPC mailed Nov. 24, 2015, for corresponding EP Application No. 14155459.2-1464, 3 pages.
Japanese Office Action dated Oct. 13, 2015, for corresponding JP Application No. 2014-229994, with English Translation, 6 pages.
European Communication under Rule 71(3) EPC, mailed Jun. 27, 2016, in corresponding European Application No. 14 155 459.2, 7 pages.
Barton, "Therapeutic potential of endothelin receptor antagonists for chronic proteinuric renal disease in humans", *Biochimica et Biophysica Acta* 1802: 1203-1213, 2010.
Dhaun et al., "Blood Pressure-Independent Reduction in Proteinuria and Arterial Stiffness After Acute Endothelin-A Receptor Antagonism in Chronic Kidney Disease", *Hypertension* 54: 113-119, 2009.
Kitiyakara et al., "Twenty-One-Year Trend in ESRD Due to Focal Segmental Glomerulosclerosis in the United States", *American Journal of Kidney Diseases* vol. 44, No. 5 (Nov.): 815-825, 2004.
Mann et al., "Avosentan for Overt Diabetic Nephropathy", *J Am Soc Nephrol* 21: 527-535, 2010.
Praga et al., "Treatment of IgA Nephropathy with ACE Inhibitors: A Randomized and Controlled Trial", *J Am Soc Nephrol* 14: 1578-1583, 2003.

(Continued)

*Primary Examiner* — Kathrien Cruz
(74) *Attorney, Agent, or Firm* — Seed IP Law Group LLP

(57) ABSTRACT

Methods of administering and pharmaceutical compositions of a biphenyl sulfonamide compound which is a dual angiotensin and endothelin receptor antagonist are disclosed for treating diseases.

4 Claims, No Drawings

(56) References Cited

OTHER PUBLICATIONS

Retrophin, Inc., "Retrophin Announces Positive Top-Line Results from Phase 2 DUET Study of Sparsentan in Patients with Focal Segmental Glomerulosclerosis", Press Release, Sep. 7, 2016, 3 pages.
Wenzel et al., "Avosentan Reduces Albumin Excretion in Diabetics with Macroalbuminuria", *J Am Soc Nephrol* 20: 655-664, 2009.
Japanese Decision of Refusal mailed Apr. 5, 2016, for corresponding Japanese Application No. 2014-229994, English Translation only, 5 pages.
Chinese Office Action dispatched Jun. 12, 2016, for corresponding CN Application No. 201410045095.9, English Translation only, 5 pages.

METHOD FOR TREATING GLOMERULOSCLEROSIS

BACKGROUND OF THE INVENTION

Field of the Invention

The present invention relates to a biphenyl sulfonamide compound which is a dual angiotensin and endothelin receptor antagonist, to pharmaceutical compositions containing such compound, to methods of manufacturing the pharmaceutical formulations containing such compound, and to methods of using such compound in the treatment of endothelin-dependent or angiotensin II-dependent disorders and other diseases.

Description of the Related Art

Angiotensin II (AngII) and endothelin-1 (ET-1) are two of the most potent endogenous vasoactive peptides currently known and are believed to play a role in controlling both vascular tone and pathological tissue remodeling associated with a variety of diseases including diabetic nephropathy, heart failure, and chronic or persistently elevated blood pressure. Currently, angiotensin receptor blockers (ARBs), which block the activity of AngII, are widely used as a treatment for diabetic nephropathy, heart failure, chronic or persistently elevated blood pressure. In addition, there is a growing body of data that demonstrates the potential therapeutic benefits of ET receptor antagonists (ERAs) in blocking ET-1 activity.

It is also known that AngII and ET-1 work together in blood pressure control and pathological tissue remodeling. For example, ARBs not only block the action of AngII at its receptor, but also limit the production of ET-1. Similarly, ERAs block ET-1 activity and inhibit the production of AngII. Consequently, simultaneously blocking AngII and ET-1 activities may offer better efficacy than blocking either substance alone.

In well-validated rat models of human chronic or persistently elevated blood pressure, the combination of an ARB and an ERA results in a synergistic effect. Furthermore, although ARBs are the standard of care for patients with diabetic nephropathy, improved efficacy with the co-administration of an ERA has been reported in Phase 2 clinical development.

There are preclinical and initial clinical data suggesting that compared to either mechanism alone, simultaneously blocking angiotensin II and endothelin 1 at their respective receptors, ATI and ETA, may provide an improved treatment option for several cardiovascular diseases.

SUMMARY OF THE INVENTION

Methods of administering, pharmaceutical dosage forms, pharmaceutical formulations, and treatment regimes of a biphenyl sulfonamide compound of the following formula I, enantiomers (including atropisomers), diastereomers, salts and metabolites thereof, methods of manufacturing the pharmaceutical formulations, and methods of using the formulations are disclosed:

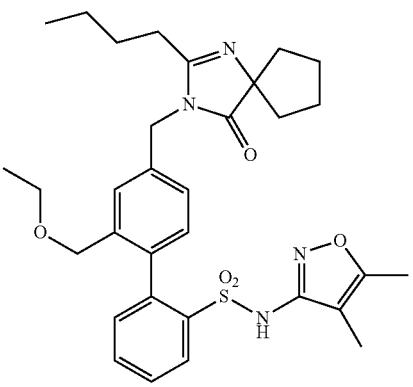

Formula I

Some embodiments provide a method of treating an endothelin-dependent or angiotensin II-dependent disorder in a subject in need thereof which comprises administering a compound of formula I or a pharmaceutically acceptable salt thereof, in an amount effective therefor. In some other embodiments, the endothelin-dependent or angiotensin II-dependent disorder is diabetic nephropathy. In some embodiments, the endothelin-dependent or angiotensin II-dependent disorder is chronic elevated blood pressure. In some embodiments, the endothelin-dependent or angiotensin II-dependent disorder is persistently elevated blood pressure. In some embodiments, the endothelin-dependent or angiotensin II-dependent disorder is hypertension.

In some embodiments, the method comprises administering a compound of formula I or a pharmaceutically acceptable salt thereof, in an amount from about 50 mg/day to about 1000 mg/day. In some embodiments, the amount of the compound of formula I, or a pharmaceutically acceptable salt thereof, administered to the human subject can be from about 200 mg/day to about 800 mg/day, more preferably about 400 mg/day, most preferably about 800 mg/day. In some embodiments, the amount of the compound of formula I, or a pharmaceutically acceptable salt thereof, administered to the human subject can be about 100 mg/day, about 200 mg/day, about 400 mg/day, or about 800 mg/day.

In some embodiments, the systolic blood pressure of the human subject is decreased to below at least 160 mmHg, below at least 140 mmHg, below at least 140 mmHg, below at least 130 mmHg, or below at least 120 mmHg. In some embodiments, the diastolic blood pressure of the human subject is decreased to below at least 120 mmHg, below at least 110 mmHg, below at least 100 mmHg, or below at least 90 mmHg. In some embodiments, the systolic or diastolic blood pressure of the human subject is decreased by at least about 5 mmHg, at least about 8 mmHg, about 10 mmHg, at least about 12 mmHg, or about 14 mmHg as compared to the systolic or diastolic blood pressure prior to treatment.

In some embodiments, the compound of formula I, or a pharmaceutically acceptable salt thereof, is administered at a frequency not greater than four times, twice, or once a day. In some embodiments, the compound of formula I, or a pharmaceutically acceptable salt thereof, is administered four times, twice, or once a day.

In some embodiments, the systolic blood pressure of less than 140 mmHg or diastolic blood pressure of less than 90 mmHg is reached within 16 weeks, within 14 weeks, within 12 weeks, within 10 weeks, or within 8 weeks of administration of the compound of compound I, or a pharmaceutically acceptable salt thereof.

Some embodiments provide a pharmaceutical composition comprising a compound of formula I, or a pharmaceutically acceptable salt thereof, for use in treating an endothelin-dependent or angiotensin II-dependent disorder in a subject in need thereof. In some embodiments, the amount of the compound of formula I or a pharmaceutically acceptable salt thereof is from about 50 mg to about 1000 mg. In some embodiments, the endothelin-dependent or angiotensin II-dependent disorder is chronic elevated blood pressure. In some embodiments, the endothelin-dependent or angiotensin II-dependent disorder is persistently elevated blood pressure. In some embodiments, the endothelin-dependent or angiotensin II-dependent disorder is diabetic nephropathy. In some embodiments, the endothelin-dependent or angiotensin II-dependent disorder is hypertension. In some embodiments, the amount of compound of formula I, or a pharmaceutically acceptable salt thereof, is from about 200 mg to about 800 mg. In some embodiments, the amount of compound of formula I, or a pharmaceutically acceptable salt thereof, is about 100 mg, about 200 mg, about 400 mg, or about 800 mg.

In some embodiments, the use of the pharmaceutical composition comprising a compound of formula I, or a pharmaceutically acceptable salt thereof, in treating the endothelin-dependent or angiotensin II-dependent disorder is decreasing the systolic blood pressure of the human subject so that it is below at least 160 mmHg, below at least 150 mmHg, below at least 140 mmHg, below at least 130 mmHg, or below at least 120 mmHg. In some embodiments, the use of the pharmaceutical composition comprising a compound of formula I, or a pharmaceutically acceptable salt thereof, in treating the endothelin-dependent or angiotensin II-dependent disorder is decreasing the diastolic blood pressure of the human subject so that it is below at least 120 mmHg, below at least 110 mmHg, below at least 100 mmHg, or below at least 90 mmHg. In some embodiments, the use of the pharmaceutical composition comprising a compound of formula I, or a pharmaceutically acceptable salt thereof, in treating the endothelin-dependent or angiotensin II-dependent disorder is decreasing the systolic or diastolic blood pressure of the human subject by at least about 5 mmHg, at least about 8 mmHg, at least about 10 mmHg, at least about 12 mmHg, or at least about 14 mmHg.

In some embodiments, the pharmaceutical composition of the compound of formula I, or a pharmaceutically acceptable salt thereof, is administered at a frequency not greater than four times, twice, or once a day. In some embodiments, the pharmaceutical composition of the compound of formula I, or a pharmaceutically acceptable salt thereof, is administered four times, twice, or once a day.

In some embodiments, the systolic blood pressure of less than 140 mmHg or diastolic blood pressure of less than 90 mmHg is reached within 16 weeks, within 14 weeks, within 12 weeks, within 10 weeks, or within 8 weeks of administration of the pharmaceutical composition of the compound of compound I, or a pharmaceutically acceptable salt thereof.

In some embodiments, the compound of formula I is provided as rapidly dissolving dosage forms. In some embodiments, the formulations have one or more of: improved friability, compression, dissolution, uniformity, dissolvability, palatability, and the like. Also, in some embodiments, the formulations can permit at least one or more of: rapid onset, greater and/or more rapid plasma levels, and the like.

Some embodiments provide a pharmaceutical composition comprising from about 100 mg to about 800 mg of the compound of formula I or a pharmaceutically acceptable salt thereof, and at least one excipient, wherein the compound of formula I comprises greater than about 35% w/w of the composition and the excipients comprise from about 5% to about 65% w/w of the composition. In some embodiments, each excipient is individually selected from the group consisting of microcrystalline cellulose, hydroxypropylcellulose, poloxamer 188, sodium starch glycolate, and croscarmellose sodium. In some embodiments, the compound of formula I is provided in an amount from about 40% to about 65% w/w of the composition, or about 50% to about 60% w/w of the composition. In some embodiments, one excipient is microcrystalline cellulose. In some embodiments, the microcrystalline cellulose can comprise from about 5% to about 65% w/w, from about 15% to about 50% w/w, from about 20% to about 40% w/w, from about 25% to about 35% w/w, or about 28% to about 30% w/w of the composition. In some embodiments, the microcrystalline cellulose is silicified microcrystalline cellulose. In some embodiments, one excipient is poloxamer 188. In some embodiments, poloxamer 188 comprises from about 0.1% to about 10% w/w, or from about 1% to about 8% w/w of the composition. In some embodiments, poloxamer 188 comprises about 5% w/w of the composition.

In some embodiments, the composition further comprises one or more lubricants, wherein the one or more lubricants comprise up to about 5% w/w of the composition. In some embodiments, the one or more lubricants are each individually selected from the group consisting of sodium lauryl sulfate, magnesium stearate, calcium stearate, sodium stearyl fumarate, stearic acid, hydrogenated vegetable oil, glyceryl behenate, and polyethylene glycol. In some embodiments, one lubricant is magnesium stearate. In some embodiments, magnesium stearate comprises from about 0.1% to about 1.5% w/w of the composition. In some embodiments, magnesium stearate comprises about 0.5% w/w or about 1.0% w/w of the composition. In some embodiments, one lubricant is sodium lauryl sulfate. In some embodiments, sodium lauryl sulfate comprises from about 0.1% to about 5% w/w, or from about 0.3% to about 2% w/w of the composition. In some embodiments, sodium lauryl sulfate comprises about 1.0% w/w of the composition. In some embodiments, the composition further comprises a glidant. In some embodiments, the glidant is colloidal silicon dioxide. In some embodiments, the colloidal silicon dioxide comprises about 0.01% to about 1.5% w/w of the composition. In some embodiments, the colloidal silicon dioxide comprises about 0.1% w/w of the composition. In some embodiments, the compound of formula I is provided in an amount of about 100 mg, or about 200 mg, or about 400 mg, or about 800 mg.

Some embodiments provide a pharmaceutical composition comprising from about 100 mg to about 800 mg of the compound of formula I, or a pharmaceutically acceptable salt thereof, and at least one excipient. In some embodiments, the excipient is selected from the group consisting of microcrystalline cellulose, lactose monohydrate, croscarmellose sodium, sodium starch glycolate, hydroxypropyl cellulose, and poloxamer 188. In some embodiments, one excipient is microcrystalline cellulose which comprises from about 20% to about 50% w/w, or from about 20% to about 40% w/w, or from about 28% to about 30% w/w of the composition. In some embodiments, the composition further comprises a glidant. In some embodiments, the composition further comprises one or more lubricants. In some embodiments, the composition further comprises one or more surfactants.

In some embodiments, the compound of formula I is provided in an amount of about 100 mg, or about 200 mg, or about 400 mg, or about 800 mg.

In some embodiments, the composition has a total weight of about 50 mg to about 1500 mg. In some embodiments, the composition has a total weight of about 50 mg, about 75 mg, about 100 mg, about 150 mg, about 175 mg, about 200 mg, about 250 mg, about 300 mg, about 350 mg, about 400 mg, about 450 mg, about 500 mg, about 550 mg, about 600 mg, about 700 mg, about 750 mg, about 800 mg, about 900 mg, about 1000 mg, about 1100 mg, about 1200 mg, about 1300 mg, about 1400 mg, or about 1500 mg.

In some embodiments, the composition is in the form of a tablet, a film coated tablet, a capsule, a gel cap, a caplet, a pellet, or a bead. In some embodiments, the composition is in the form of a film coated tablet.

Some embodiments provides a tablet comprising from about 100 mg to about 800 mg the compound of formula I or a pharmaceutically acceptable salt thereof, the tablets having a hardness of at least about 4 Kp. In some embodiments, the tablet has a hardless of at least about 6 Kp, or at least about 8 Kp, or at least about 10 Kp, or at least about 12 Kp, or at least about 14 Kp. In some embodiments, the tablet has a hardness of about 4 Kp, about 6 Kp, about 8 Kp, about 10 Kp, about 12 Kp, about 14 Kp, or about 16 Kp.

Some embodiments provide a pharmaceutical composition comprising from about 100 mg to about 800 mg of the compound of formula I, or a pharmaceutically acceptable salt thereof, wherein the composition having at least an 85 percent release of the compound of formula I, or the salt of the compound of formula I, within 45 minutes using U.S. Pharmacopeia (USP) type II dissolution Apparatus I at 50 rpm or 60 rpm in 0.1N HCl. In some embodiments, the composition has at least an 85 percent release rate at 30 minutes, or at 20 minutes, or at 15 minutes. In some embodiments, the composition has at least a 90 percent release rate at 30 minutes. In some embodiments, the composition has at least a 95 percent release rate at 30 minutes.

Some embodiments provide a method of treating chronic or persistently elevated blood pressure, comprising identifying an individual in need of such treatment, and administering the pharmaceutical compositions of the compound of formula I.

Some embodiments provide a method of making a pharmaceutical composition comprising blending together from about 100 mg to about 800 mg of the compound of formula I, and one or more excipients, wherein the one or more excipients comprise from about 5% to about 65% w/w of the composition. In some embodiments, one excipient is microcrystalline cellulose. In some embodiments, the microcrystalline cellulose comprises from about 20% to about 50% w/w, or from about 28% to about 30% w/w of the composition. In some embodiments, the method further comprises adding from about 0.5% to about 1.0% w/w magnesium stearate. In some embodiments, the method further comprises adding about 5% w/w poloxamer 188. In some embodiments, the method further comprises adding about 1.0% w/w sodium lauryl sulfate. In some embodiments, the method further comprises adding about 0.1% w/w colloidal silicon dioxide. In some embodiments, the compound of formula I is provided in an amount of about 100 mg, or about 200 mg, or about 400 mg, or about 800 mg.

Some embodiments provide a pharmaceutical composition comprising from about 100 mg to about 800 mg of the compound of formula I, or a pharmaceutically acceptable salt thereof, and microcrystalline cellulose which comprises about 29% w/w of the composition, croscarmellose sodium which comprises about 5% w/w of the composition, hydroxypropylcellulose which comprises about 3% w/w of the composition, poloxamer 188 which comprises about 5% w/w of the composition, colloidal silicone dioxide which comprises about 0.1% w/w of the composition, and magnesium stearate which comprises about 0.5% w/w of the composition.

Some embodiments provide a pharmaceutical composition comprising from about 100 mg to about 800 mg of the compound of formula I, or a pharmaceutically acceptable salt thereof, and microcrystalline cellulose which comprises about 22% w/w of the composition, lactose monohydrate which comprises about 11% w/w of the composition, sodium lauryl sulfate which comprises about 1% w/w of the composition, croscarmellose sodium which comprises about 5% w/w of the composition, hydroxypropylcellulose which comprises about 3.0% w/w of the composition, colloidal silicone dioxide which comprises about 0.1% w/w of the composition, and magnesium stearate which comprises about 1% w/w of the composition.

Some embodiments provide a pharmaceutical composition comprising from about 100 mg to about 800 mg of the compound of formula I, or a pharmaceutically acceptable salt thereof, and microcrystalline cellulose which comprises about 29% w/w of the composition, croscarmellose sodium which comprises about 5% w/w of the composition, hydroxypropylcellulose which comprises about 3% w/w of the composition, poloxamer 188 comprises about 5% w/w of the composition, colloidal silicone dioxide which comprises about 0.1% w/w of the composition, and magnesium stearate which comprises about 1% w/w of the composition.

Some embodiments provide a pharmaceutical composition comprising from about 100 mg to about 800 mg of the compound of formula I, or a pharmaceutically acceptable salt thereof, and microcrystalline cellulose which comprises about 33% w/w of the composition, sodium lauryl sulfate which comprises about 1% w/w of the composition, croscarmellose sodium which comprises about 5% w/w of the composition, hydroxypropylcellulose which comprises about 3% w/w of the composition, colloidal silicone dioxide which comprises about 0.1% w/w of the composition, and magnesium stearate which comprises about 1% w/w of the composition.

Some embodiments provide a pharmaceutical composition comprising from about 100 mg to about 800 mg of the compound of formula I, or a pharmaceutically acceptable salt thereof, and microcrystalline cellulose which comprises about 29% w/w of the composition, hydroxypropylcellulose which comprises about 3% w/w of the composition, poloxamer 188 which comprises about 5% w/w of the composition, sodium starch glycolate which comprises about 5% w/w of the composition, colloidal silicone dioxide which comprises about 0.1% w/w of the composition, and magnesium stearate which comprises about 1% w/w of the composition.

DETAILED DESCRIPTION OF THE PREFERRED EMBODIMENT

The following are definitions of terms used in this specification. The initial definition provided for a group or term herein applies to that group or term throughout the present specification, individually or as part of another group, unless otherwise indicated.

The compound of formula I form salts which are also within the scope of this disclosure. Reference to a compound of formula I herein is understood to include reference to salts thereof, unless otherwise indicated. The term "salt(s)", as employed herein, denotes acidic and/or basic salts formed with inorganic and/or organic acids and bases. In addition, when the compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compound of formula I may be formed, for example, by reacting the compound of formula I with an amount of acid or base, such as an equivalent amount, in a medium such as one in which the salt precipitates or in an aqueous medium followed by lyophilization.

The compound of formula I which contains a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compound of formula I which contains an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compound of formula I are also contemplated. The term "prodrug" denotes a compound which, upon administration to a subject, undergoes chemical conversion by metabolic or chemical processes to yield a compound of formula I, or a salt and/or solvate thereof. Solvates of the compound of formula I are preferably hydrates. Any tautomers are also contemplated.

All stereoisomers of the compound of formula I, such as those which may exist due to asymmetric carbons on the R substituents, including enantiomeric forms (which may exist even in the absence of asymmetric carbons, e.g., atropisomers) and diastereomeric forms, are contemplated. Individual stereoisomers of the compound of formula I may, for example, be substantially free of other isomers, or may be admixed, for example, as racemates or with all other, or other selected, stereoisomers. The chiral centers of the compound of formula I can have the S or R configuration.

Methods of Preparation

The compound of formula I may be prepared by methods such as those illustrated in the following Schemes I to II. Solvents, temperatures, pressures, and other reaction conditions may be selected by one of ordinary skill in the art.

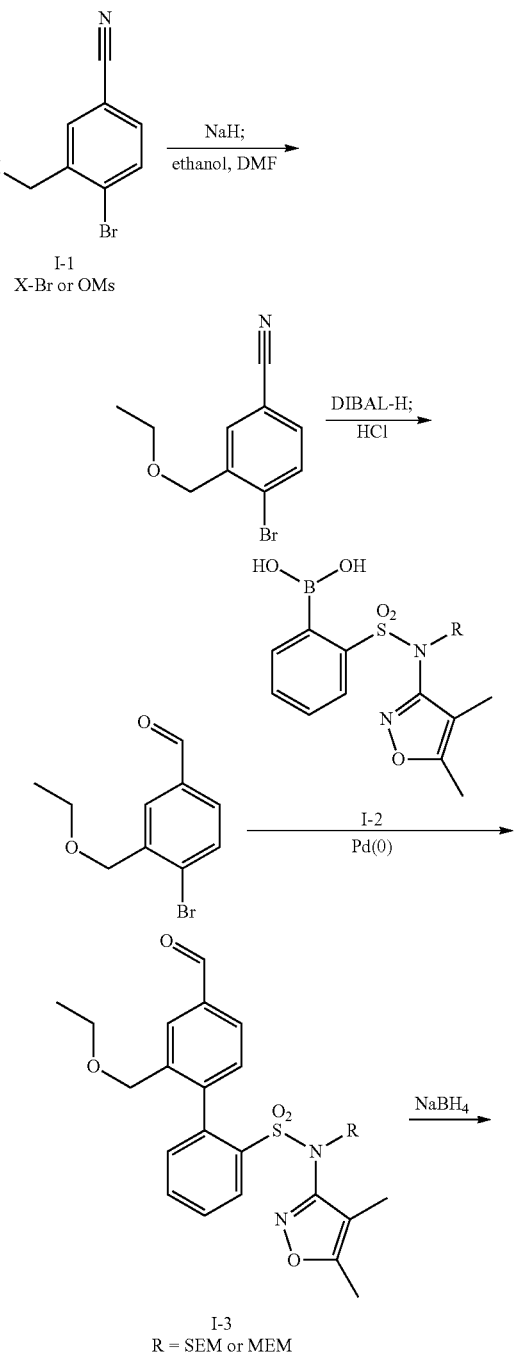

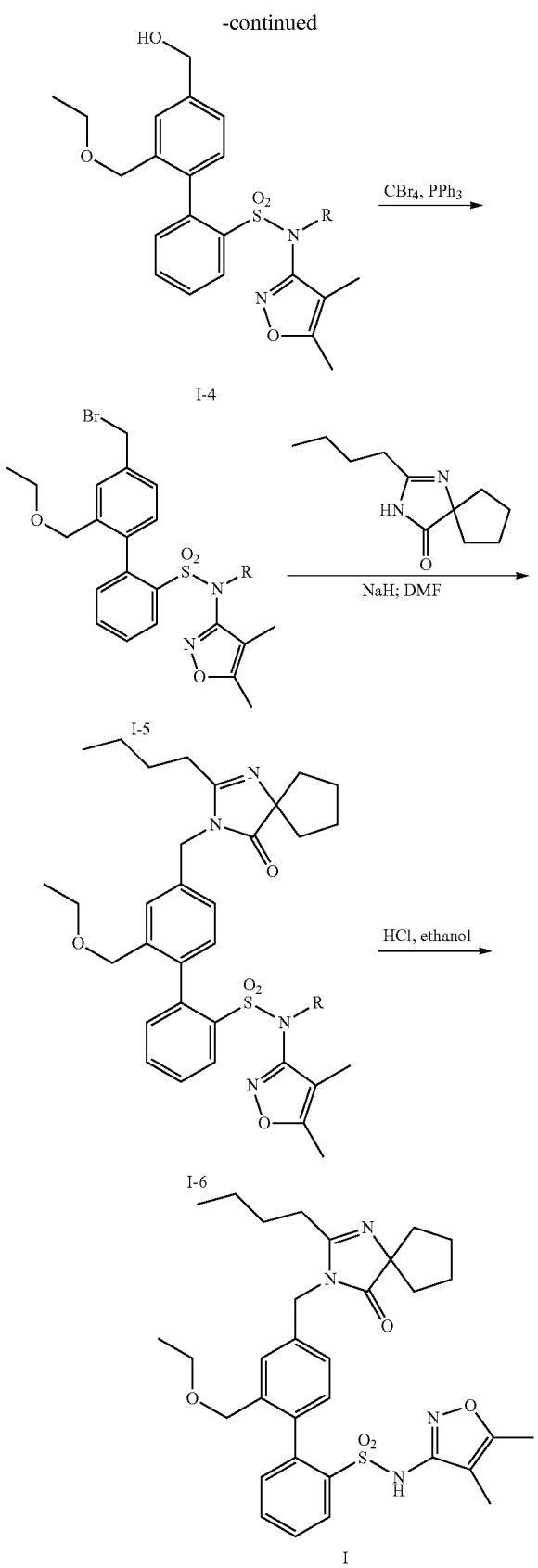

tuted 4-bromobenzonitrile formula I-1 (X is bromine or mesylate) can be treated sodium ethoxide in DMF, for example ethyl alcohol in DMF can be treated with sodium hydride, to provide 4-bromo-3-(ethoxymethyl)benzonitrile. 4-Bromo-3-(ethoxymethyl)benzonitrile can be converted to 4-bromo-3-(ethoxymethyl)benzaldehyde by reduction of the nitrile to an aldehyde. For example, 4-bromo-3-(ethoxymethyl)benzonitrile can be treated with DIBAL-H followed by methanol and hydrochloric acid to provide 4-bromo-3-(ethoxymethyl)benzaldehyde. The 4-bromo-3-(ethoxymethyl)benzaldehyde can then be coupled with a compound of formula I-2 in the presence of a palladium catalyst, for example tetrakis(triphenylphosphine) palladium(0), under the appropriate conditions to provide a compound of formula I-3 (R is SEM or MEM). The aldehyde of the compound of formula I-3 can be reduced to an alcohol thereby providing a compound of formula I-4. For example, the compound of formula I-3 can be treated with sodium borohydride in ethyl alcohol or methyl alcohol to provide the compound of formula I-4 (R is SEM or MEM). The benzyl alcohol of formula I-4 can then be converted to a benzyl bromide thereby providing a compound of formula I-5 (R is SEM or MEM). For example, benzyl alcohol of formula I-4 in DMF in the presence of carbon tetrabromide can be treated with triphenyl phosphine to provide benzyl bromide of formula I-5. The benzyl bromide of formula I-5 can be treated with 2-N-butyl-1,3-diazaspiro[4.4]non-1-en-4-one hydrochloride to provide the compound of formula I-6 (R is SEM or MEM). For example, 2-N-butyl-1,3-diazaspiro[4.4]non-1-en-4-one hydrochloride can be treated with sodium hydride in DMF followed by addition of the benzyl bromide of formula I-5 to provide the compound of formula I-6. The compound of formula I-6 can be deprotected under acidic conditions, for example the compound of formula I-6 in ethyl alcohol can be treated with 6N hydrochloric acid, thereby providing the compound of formula I, 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide.

Scheme II

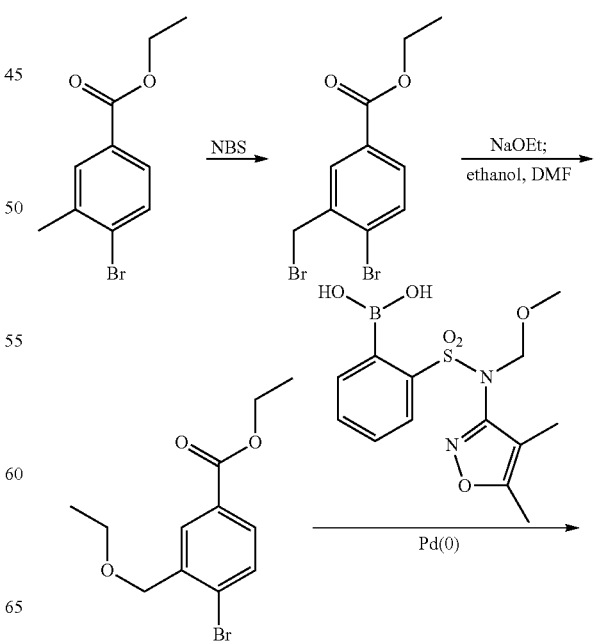

In one embodiment, the compound of formula I can be synthesized by the method disclosed in Scheme I. Substi-

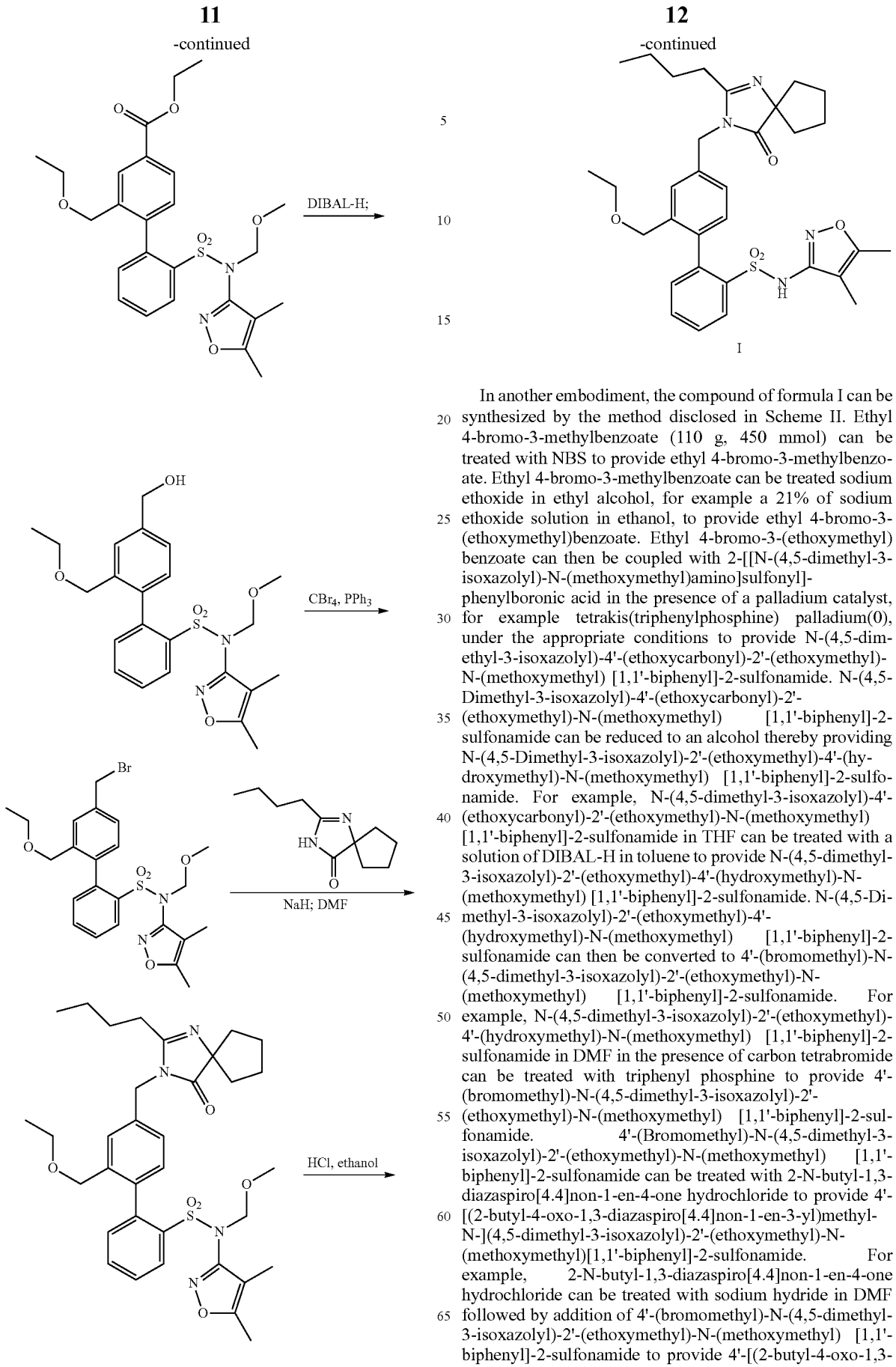

In another embodiment, the compound of formula I can be synthesized by the method disclosed in Scheme II. Ethyl 4-bromo-3-methylbenzoate (110 g, 450 mmol) can be treated with NBS to provide ethyl 4-bromo-3-methylbenzoate. Ethyl 4-bromo-3-methylbenzoate can be treated sodium ethoxide in ethyl alcohol, for example a 21% of sodium ethoxide solution in ethanol, to provide ethyl 4-bromo-3-(ethoxymethyl)benzoate. Ethyl 4-bromo-3-(ethoxymethyl) benzoate can then be coupled with 2-[[N-(4,5-dimethyl-3-isoxazolyl)-N-(methoxymethyl)amino]sulfonyl]-phenylboronic acid in the presence of a palladium catalyst, for example tetrakis(triphenylphosphine) palladium(0), under the appropriate conditions to provide N-(4,5-dimethyl-3-isoxazolyl)-4'-(ethoxycarbonyl)-2'-(ethoxymethyl)-N-(methoxymethyl) [1,1'-biphenyl]-2-sulfonamide. N-(4,5-Dimethyl-3-isoxazolyl)-4'-(ethoxycarbonyl)-2'-(ethoxymethyl)-N-(methoxymethyl) [1,1'-biphenyl]-2-sulfonamide can be reduced to an alcohol thereby providing N-(4,5-Dimethyl-3-isoxazolyl)-2'-(ethoxymethyl)-4'-(hydroxymethyl)-N-(methoxymethyl) [1,1'-biphenyl]-2-sulfonamide. For example, N-(4,5-dimethyl-3-isoxazolyl)-4'-(ethoxycarbonyl)-2'-(ethoxymethyl)-N-(methoxymethyl) [1,1'-biphenyl]-2-sulfonamide in THF can be treated with a solution of DIBAL-H in toluene to provide N-(4,5-dimethyl-3-isoxazolyl)-2'-(ethoxymethyl)-4'-(hydroxymethyl)-N-(methoxymethyl) [1,1'-biphenyl]-2-sulfonamide. N-(4,5-Dimethyl-3-isoxazolyl)-2'-(ethoxymethyl)-4'-(hydroxymethyl)-N-(methoxymethyl) [1,1'-biphenyl]-2-sulfonamide can then be converted to 4'-(bromomethyl)-N-(4,5-dimethyl-3-isoxazolyl)-2'-(ethoxymethyl)-N-(methoxymethyl) [1,1'-biphenyl]-2-sulfonamide. For example, N-(4,5-dimethyl-3-isoxazolyl)-2'-(ethoxymethyl)-4'-(hydroxymethyl)-N-(methoxymethyl) [1,1'-biphenyl]-2-sulfonamide in DMF in the presence of carbon tetrabromide can be treated with triphenyl phosphine to provide 4'-(bromomethyl)-N-(4,5-dimethyl-3-isoxazolyl)-2'-(ethoxymethyl)-N-(methoxymethyl) [1,1'-biphenyl]-2-sulfonamide. 4'-(Bromomethyl)-N-(4,5-dimethyl-3-isoxazolyl)-2'-(ethoxymethyl)-N-(methoxymethyl) [1,1'-biphenyl]-2-sulfonamide can be treated with 2-N-butyl-1,3-diazaspiro[4.4]non-1-en-4-one hydrochloride to provide 4'-[(2-butyl-4-oxo-1,3-diazaspiro[4.4]non-1-en-3-yl)methyl-N-](4,5-dimethyl-3-isoxazolyl)-2'-(ethoxymethyl)-N-(methoxymethyl)[1,1'-biphenyl]-2-sulfonamide. For example, 2-N-butyl-1,3-diazaspiro[4.4]non-1-en-4-one hydrochloride can be treated with sodium hydride in DMF followed by addition of 4'-(bromomethyl)-N-(4,5-dimethyl-3-isoxazolyl)-2'-(ethoxymethyl)-N-(methoxymethyl) [1,1'-biphenyl]-2-sulfonamide to provide 4'-[(2-butyl-4-oxo-1,3- diazaspiro[4.4]non-1-en-3-yl)methyl-N-](4,5-dimethyl-3-isoxazolyl)-2'-(ethoxymethyl)-N-(methoxymethyl) [1,1'-biphenyl]-2-sulfonamide. 4'-[(2-Butyl-4-oxo-1,3-diazaspiro[4.4]non-1-en-3-yl)methyl-N-](4,5-dimethyl-3-isoxazolyl)-2'-(ethoxymethyl)-N-(methoxymethyl) [1,1'-biphenyl]-2-sulfonamide can be deprotected under acidic conditions, thereby providing the compound of formula I, 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide. For example 4'-[(2-Butyl-4-oxo-1,3-diazaspiro[4.4]non-1-en-3-yl)methyl-N-](4,5-di methyl-3-isoxazolyl)-2'-(ethoxymethyl)-N-(methoxymethyl) [1,1'-biphenyl]-2-sulfonamide in ethyl alcohol can be treated with 6N hydrochloric acid to provide the compound of formula I, 4'-[(2-Butyl-4-oxo-1,3-diazaspiro[4.4]non-1-en-3-yl) methyl]-N-(4,5-dimethyl-3-isoxazolyl)-2'-(ethoxymethyl) [1,1'-biphenyl]-2-sulfonamide.

The compound of formula I and salts thereof are antagonists of both endothelin (especially, ET-1) and angiotensin II (especially, subtype $AT_1$) receptors ("dual angiotensin endothelin receptor antagonists") and are useful in treatment of conditions associated with increased ET levels and/or increased angiotensin II levels and of all endothelin-dependent or angiotensin II-dependent disorders. They are thus useful as antihypertensive agents. By the administration of a composition having the compound of formula I, the blood pressure of a hypertensive mammalian (e.g., human) host is reduced. They are also useful in portal chronic or persistently elevated blood pressure, chronic or persistently elevated blood pressure secondary to treatment with erythropoietin, low renin chronic or persistently elevated blood pressure, and chronic or persistently elevated blood pressure.

The compound of formula I is also useful in the treatment of disorders related to renal, glomerular and mesangial cell function, including acute (such as ischemic, nephrotoxic, or glomerulonephritis) and chronic (such as diabetic, hypertensive or immune-mediated) renal failure, diabetic nephropathy, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compound of formula I is also useful in the treatment of disorders related to paracrine and endocrine function. The compound of formula I is also useful in the treatment of diabetic nephropathy, IGA-induced nephropathy, and hypertension-induced nephropathy. The term "diabetic nephropathy" as used herein will be understood to include both incipient and overt stages of diabetic nephropathy, whether diagnosed or not, but most typically as diagnosed by a clinician or physician.

The compound of formula I is also useful in the treatment of endotoxemia or endotoxin shock as well as hemorrhagic shock. The compound of formula I is also useful in alleviation of pain associated cancer, such as the pain associated with prostate cancer, and bone pain associated with bone cancer. The compound of formula I is further useful in the prevention and/or reduction of end-organ damage associated the cell-proliferative effects of endothelin.

The compound of formula I is also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compound of formula I is also useful as anti-arrhythmic agents; anti-anginal agents; anti-fibrillatory agents; anti-asthmatic agents; anti-atherosclerotic and anti-arteriosclerotic agents (including anti-transplantation arteriosclerotic agents); additives to cardioplegic solutions for cardiopulmonary bypasses; adjuncts to thrombolytic therapy; and anti-diarrheal agents. The compound of formula I may be useful in therapy for myocardial infarction; therapy for peripheral vascular disease (e.g., Raynaud's disease, intermittent claudication and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer, inflammatory bowel disease and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedure including transplantation and stenting; therapy for congestive heart failure including inhibition of fibrosis; inhibition of left ventricular dilatation, remodeling and dysfunction; and treatment of hepatotoxicity and sudden death. The compound of formula I is useful in the treatment of sickle cell disease including the initiation and/or evolution of the pain crises of this disease; treatment of the deleterious consequences of ET-producing tumors such as chronic or persistently elevated blood pressure resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compound of formula I is useful in therapy for metabolic and neurological disorders; cancer; insulin-dependent and non insulin-dependent diabetes mellitus; neuropathy; retinopathy; epilepsy; hemorrhagic and ischemic stroke; bone remodeling; psoriasis; and chronic inflammatory diseases such as arthritis, rheumatoid arthritis, osteoarthritis, sarcoidosis and eczematous dermatitis (all types of dermatitis).

The compound of formula I is additionally useful in the treatment of disorders involving bronchoconstriction and disorders of chronic or acute pulmonary inflammation such as chronic obstructive pulmonary disease (COPD) and adult respiratory distress syndrome (ARDS).

The compound of formula I is also useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum.

The compound of formula I is also useful in the treatment of dementia, including Alzheimer's dementia, senile dementia and vascular dementia. Additionally, the compound of formula I is further useful in the reduction of general morbidity and/or mortality as a result of the above utilities. Methods for the treatment of all endothelin-dependent or angiotensin II-dependent disorders, comprising the step of administering to a subject in need thereof the compound of formula I in an amount effective therefore are provided. Other therapeutic agents such as those described below may be employed with the compound of formula I in the present methods. In the methods, such other therapeutic agent(s) may be administered prior to, simultaneously with or following the administration of the compound of formula I of the present disclosure.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compound of formula I may be found in "Remington's Pharmaceutical Sciences," Mack Publishing Co., Easton, Pa., 18th edition, 1990.

Some embodiments provide low-dose the compound of formula I in tablets, film coated tablets, capsules, caplets, pills, gel caps, pellets, beads, or dragee dosage forms. Preferably, the formulations disclosed herein can provide favorable drug processing qualities, including, for example, but not limited to, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

In other embodiments, the formulation yields a rapidly dissolving dosage form, for which at least 85% of the labeled amount of the drug substance dissolves within 45 minutes, using *U.S. Pharmacopeia* (USP) type II dissolution Apparatus utilizing 0.1N HCl at 37° C. with 50 rpm paddle speed. In other embodiments, the formulation yields a rapidly dissolving dosage form, for which at least 85% of the labeled amount of the drug substance dissolves within 45 minutes, using *U.S. Pharmacopeia* (USP) type II dissolution Apparatus utilizing 0.1N HCl at 37° C. with 60 rpm paddle speed. In other embodiments, the formulation yields a rapidly dissolving dosage form, for which at least 85% of the labeled amount of the drug substance dissolves within 30 minutes, using *U.S. Pharmacopeia* (USP) type II dissolution Apparatus utilizing 0.1N HCl at 37° C. with 50 rpm paddle speed. In other embodiments, the formulation yields a rapidly dissolving dosage form, for which at least 85% of the labeled amount of the drug substance dissolves within 30 minutes, using *U.S. Pharmacopeia* (USP) type II dissolution Apparatus utilizing 0.1N HCl at 37° C. with 50 rpm paddle speed. In other embodiments, the formulation yields a rapidly dissolving dosage form, for which at least 85% of the labeled amount of the drug substance dissolves within 20 minutes, using *U.S. Pharmacopeia* (USP) type II dissolution Apparatus utilizing 0.1N HCl at 37° C. with 50 rpm paddle speed. In other embodiments, the formulation yields a rapidly dissolving dosage form, for which at least 85% of the labeled amount of the drug substance dissolves within 20 minutes, using *U.S. Pharmacopeia* (USP) type II dissolution Apparatus utilizing 0.1N HCl at 37° C. with 50 rpm paddle speed.

In some embodiments, the formulations require minimal tablet compression forces to achieve a hardness of about 2 kp to about 25 kp. In some aspects, the formulation can require compression forces to achieve a hardness of, for example, at least about 2, 3, 4, 5, 6, 7, 8, 9, 10, 11, 12, 13, 14, 15, 16, 17, 18, 19, 20, 21, or 22 kp. Such minimal compression forces can enables the tablets to remain relatively porous and disintegrate fast with minimal wear on compression tooling and the tablet press.

In other embodiments, the formulations can yield tablets, including film coated tablets, having a friability value of 1% or less. Thus, in some embodiments, the friability value is about 0.9%, 0.8%, 0.75%, 0.6%, 0.5%, 0.4%, 0.3%, 0.25%, 0.2%, 0.15%, 0.1%, 0.08%, 0.06%, 0.04%, 0.02% or less.

The compound of formula I can be formulated readily, for example, by combining the drug substance with any suitable pharmaceutically acceptable excipient(s) for example, but not limited to, binders, diluents, disintegrants, lubricants, fillers, carriers, coatings, glidants, flavours, color additives, and the like, as set forth below. Such compositions can be prepared for storage and for subsequent processing.

Excipients

Acceptable excipients for therapeutic use are well known in the pharmaceutical art, and are described, for example, in Handbook of Pharmaceutical Excipients, 5th edition (Raymond C Rowe, Paul J Sheskey and Siân C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. Excipients can include, by way of illustration and not limitation, diluents, disintegrants, binding agents, wetting agents, polymers, lubricants, glidants, coatings, sweetens, solubilizing agens substances added to mask or counteract a disagreeable taste or odor, flavors, colorants, fragrances, and substances added to improve appearance of the composition.

Acceptable excipients include, for example, but are not limited to, microcrystalline cellulose, lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose monohydrate, lecithin, albumin, sodium glutamate, cysteine hydrochloride, croscarmellose sodium, sodium starch glycolate, hydroxypropyl cellulose, poloxamer (e.g., poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, 407, and poloxamer 105 benzoate, poloxamer 182 dibenzoate 407, and the like), sodium lauryl sulfate, colloidal silicon dioxide and the like. Examples of suitable excipients for tablets and capsules include, but are not limited to, microcrystalline cellulose, silicified microcrystalline cellulose, lactose monohydrate, croscarmellose sodium, sodium starch, hydroxypropyl cellulose, poloxamer 188, sodium lauryl sulfate, colloidal silicon dioxide, magnesium stearate. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. The compound can also be made in microencapsulated form. If desired, absorption enhancing preparations (for example, liposomes), can be utilized.

The compositions and formulations can include any other agents that provide improved transfer, delivery, tolerance, and the like. These compositions and formulations can include, for example, powders, pastes, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures can be appropriate in treatments and therapies in accordance with the disclosure herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J. Pharm. Sci. 89(8):967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein.

As will be appreciated by those of skill in the art, the amounts of excipients will be determined by drug dosage and dosage form size. In some embodiments disclosed herein, the dosage form size is about 175 mg. In some embodiment disclosed here in the dosage form size is about 350 mg. In some embodiment disclosed here in the dosage form size is about 700 mg. This dosage form weight is arbitrary and one skilled in the art will realize that a range of weights can be made and are encompassed by this disclosure. The preferred dosage form range is from about 50 mg to about 1500 mg, more typically from about 100 mg to about 1000 mg, more typically from about 175 mg to abpit 700 mg, with the preferred typical form weight being about 175 mg, about 350 mg, or about 700 mg.

Lubricants

In some embodiments, lubricants are employed in the manufacture of certain dosage forms. For example, a lubricant will often be employed when producing tablets. In some embodiments, a lubricant can be added just before the tableting step, and can be mixed with the formulation for a minimum period of time to obtain good dispersal. In some embodiments, one or more lubricants can be used. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate and mixtures of magnesium stearate with sodium lauryl sulfate. Lubricants can comprise from about 0.25% to about 50% of the tablet weight, typically from about 1% to about 40%, more typically from about 5% to about 30%, most typically from 20% to 30%. In some embodiments, magnesium stearate can be added as a lubricant, for example, to improve powder flow, prevent the blend from adhering to tableting equipment and punch surfaces and provide lubrication to allow tablets to be cleanly ejected from tablet dies. Magnesium stearate can typically be added to pharmaceutical formulations at concentrations ranging from about 0.1% to about 5.0% w/w, or from about 0.25% to about 4% w/w, or from about 0.5% % to about 3% w/w, or from about 0.75% to about 2% w/w, or from about 0.8% to about 1.5% w/w, or from about 0.85% to about 1.25% w/w, or from about 0.9% to about 1.20% w/w, or from about 0.85% to about 1.15% w/w, or from about 0.90% to about 1 w/w, or from about 0.95% to about 1.05% w/w, or from about 0.95% to about 1% w/w. The above ranges are examples of typical ranges. One of ordinary skill in the art would recognize additional lubricants and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of lubricant(s) added in order to keep the overall unit weight of the tablet unchanged.

Color Additives

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current disclosure.

Binders

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), hydroxypropyl cellulose (HPC), and the like. Accordingly, in some embodiments, the formulations disclosed herein can include at least one binder to enhance the compressibility of the major excipient(s). For example, the formulation can include at least one of the following binders in the following preferred ranges: from about 2% to about 6% w/w hydroxypropyl cellulose (Klucel), from about 2% to about 5% w/w polyvinylpyrrolidone (PVP), from about 1% to about 5% w/w methylcellulose, from about 2% to about 5% hydroxypropyl methylcellulose, from about 1% to about 5% w/w ethylcellulose, from about 1% to about 5% w/w sodium carboxy methylcellulose, and the like. The above ranges are exemplary preferred ranges. One of ordinary skill in the art would recognize additional binders and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of binder added in order to keep the overall unit weight of the tablet unchanged. In one embodiment, the binder(s) is(are) sprayed on from solution, e.g. wet granulation, to increase binding activity.

Disintegrants

In some embodiments, disintegrants are used, for example, to facilitate tablet disintegration after administration, and are generally starches, clays, celluloses, algins, gums, or crosslinked polymers. Suitable disintegrants include, but are not limited to, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like.

The above ranges are examples of preferred ranges. One of ordinary skill in the art would recognize additional disintegrants and/or amounts of disintegrants that can be used in the formulations described herein. As would be recognized by one of ordinary skill in the art, when incorporated into the formulations disclosed herein, the amounts of the major filler(s) and/or other excipients can be reduced accordingly to accommodate the amount of disintegrant added in order to keep the overall unit weight of the tablet unchanged.

Coatings

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

Diluents

In some embodiments, diluents are used, and are generally selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt and glycerol, polydextrose, starch, or the like, or any mixture thereof.

Surfactants

In some embodiments, surfactants are used. The use of surfactants as wetting agents in oral drug forms is described in the literature, for example in H. Sucker, P. Fuchs, P. Speiser, Pharmazeutische Technologie, 2nd edition, Thieme 1989, page 260. It is known from other papers, such as published in Advanced Drug Delivery Reviews (1997), 23, pages 163-183, that it is also possible to use surfactants, inter alia, to improve the permeation and bioavailability of pharmaceutical active compounds. Examples of surfactants include, but are not limited to, anionic surfactants, non-ionic surfactants, zwitterionic surfactants and a mixture thereof. Preferably, the surfactants is selected from the group consisting of poly(oxyethylene) sorbitan fatty acid ester, poly (oxyethylene) stearate, poly(oxyethylene) alkyl ether, polyglycolated glyceride, poly(oxyethylene) caster oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

Glidants

In some embodiments, glidants are used. Examples of glidants which may be used include, but are not limited to, colloidal silicon dioxide, magnesium trisilicate, powdered cellulose, starch, talc and calcium phosphate, or the like, and mixtures thereof.

The above excipients can be present in amount up to about 95% of the total composition weight, or up to about 85% of the total composition weight, or up to about 75% of the total composition weight, or up to about 65% of the total composition weight, or up to about 55% of the total composition weight, or up to about 45% of the total composition weight, or up to about 43% of the total composition weight, or up to about 40% of the total composition weight, or up to about 35% of the total composition weight, or up to about 30% of the total composition weight, or up to about 25% of the total composition weight, or up to about 20% of the total composition weight, or up to about 15% of the total composition weight, or up to about 10% of the total composition weight, or less.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound of formula I can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present disclosure may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present disclosure thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compound of formula I can be formulated readily by combining the active compound with pharmaceutically acceptable carriers well known in the art. Such carriers enable the compound of formula I to be formulated as tablets, film coated tablets, pills, dragees, capsules, liquids, gels, get caps, pellets, beads, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. In addition, stabilizers can be added. All formulations for oral administration should be in dosages suitable for such administration. In some embodiments, formulations of the compound of formula I with an acceptable immediate release dissolution profile and a robust, scalable method of manufacture are disclosed.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compound of formula I is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delviery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound of formula I may also be formulated in rectal compositions such as suppositories or retention enemas, e.g., containing conventional suppository bases such as cocoa butter or other glycerides.

In addition to the formulations described previously, the compound of formula I may also be formulated as a depot preparation. Such long acting formulations may be administered by implantation (for example subcutaneously or intramuscularly) or by intramuscular injection. Thus, for example, the compound of formula I may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compound of formula I or pharmaceutical compositions may be administered to the patient by any suitable means. Non-limiting examples of methods of administration include, among others, (a) administration though oral pathways, which includes administration in capsule, tablet, granule, spray, syrup, or other such forms; (b) administration through non-oral pathways such as rectal, vaginal, intraurethral, intraocular, intranasal, or intraauricular, which includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of formula I into contact with living tissue.

Pharmaceutical compositions suitable for administration include compositions where the compound of formula I is contained in an amount effective to achieve its intended purpose. The therapeutically effective amount of the compound of formula I disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, and the specific use for which the compound of formula I are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compound of formula I may be administered orally or via injection at a dose from 0.001 to 2500 mg/kg of the patient's body weight per day. The dose range for adult humans is generally from 0.01 mg to 10 g/day. Tablets or other forms of presentation provided in discrete units may conveniently contain an amount of the compound of formula I which is effective at such dosage or as a multiple of the same, for instance, units containing 5 mg to 1000 mg, usually from about 100 mg to about 800 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The exact formulation, route of administration and dosage for the pharmaceutical compositions of the compound of formula I can be chosen by the individual physician in view of the patient's condition. (See, e.g., Fingl et al. 1975, in "The Pharmacological Basis of Therapeutics," which is hereby incorporated herein by reference, with particular reference to Ch. 1). Typically, the dose range of the composition administered to the patient can be from about 0.01 to about 1000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and about 500%, more preferably between about 25% and about 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 1500 mg, e.g., 5 to 1000 mg. In other embodiments, an oral dose of each active ingredient of between 1 mg and 1000 mg, preferably between 50 mg and 900 mg, e.g., 100 to 800 mg is used. In cases of administration of a pharmaceutically acceptable salt, dosages may be calculated as the free base. In some embodiments, the composition is administered 1 to 4 times per day. Alternatively the compositions of the compound of formula I may be administered by continuous intravenous infusion, preferably at a dose of each active ingredient up to 1000 mg per day. As will be understood by those of skill in the art, in certain situations it may be necessary to administer the compound disclosed herein in amounts that exceed, or even far exceed, the above-stated, preferred dosage range in order to effectively and aggressively treat particularly aggressive diseases or infections. In some embodiments, the compound of formula I will be administered for a period of continuous therapy, for example for a week or more, or for months or years.

In some embodiments, the dosing regimen of the compound of formula I is administered for a period of time, which time period can be, for example, from at least about 4 weeks to at least about 8 weeks, from at least about 4 weeks to at least about 12 weeks, from at least about 4 weeks to at least about 16 weeks, or longer. The dosing regimen of the compound of formula I can be administered three times a day, twice a day, daily, every other day, three times a week, every other week, three times per month, once monthly, substantially continuously or continuously.

Some embodiments provide a method to use an effective amount of the compound of formula I in the treatment of endothelin-dependent or angiotensin II-dependent disorders in a patient comprising administering to the patient a dosage of the compound of formula I containing an amount of about 10 mg to about 1000 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 100 mg to about 1000 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 100 mg to about 900 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 100 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 200 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 400 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 800 mg, of drug per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 0.01 mg to about 1000 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 0.1 mg to about 500 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 0.1 mg to about 100 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 0.5 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 1 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 5 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 25 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Some embodiments provide a method to use an effective amount of the compound of formula I in the treatment of endothelin-dependent or angiotensin II-dependent disorders in a patient comprising administering to the patient a dosage of the compound of formula I containing an amount of about 50 mg of drug per kilogram of body weight per dose of the compound of formula I, orally, three times per month, once monthly, once weekly, once every three days, once every two days, once per day, twice per day, or three times per day substantially continuously or continuously, for the desired duration of treatment.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. In some embodiments, compositions can be administered using a regimen which maintains plasma levels above the MEC for 10-90% of the time, for example, between 15-30%, 20-45%, 25-50%, 30-55%, 35-60%, 40-65%, 45-70%, 50-75%, 55-80%, 60-90%, 65-75%, 70-80% x, 75-85%, 15-90%, 20-90%, 25-90%, 30-90%, 35-90%, 40-90%, 45-90%, 50-90%, 55-90%, 60-90%, 65-90%, 70-90%, 75-90%, or 80-90%. In some embodiments, compositions can be administered using a regimen which maintains plasma levels above the MEC for 20-90% of the time. In some embodiments, compositions can be administered using a regimen which maintains plasma levels above the MEC for 30-90% of the time, between 40-90% and most typically between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

The compound of formula I disclosed herein can be evaluated for efficacy and toxicity using known methods. For example, the toxicology of the compound of formula I may be established by determining in vitro toxicity towards a cell line, such as a mammalian, and preferably human, cell line. The results of such studies are often predictive of toxicity in animals, such as mammals, or more specifically, humans. Alternatively, the toxicity of the compound of formula I in an animal model, such as mice, rats, rabbits, or monkeys, may be determined using known methods. The efficacy of the compound of formula I may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound of formula I formulated in a compatible pharmaceutical carrier may also be prepared, placed in an appropriate container, and labeled for treatment of an indicated condition.

An effective amount of the compound of formula I may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 100 to about 800 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

Pharmaceutical compositions comprising the compound of formula I capable of treating an endothelin-dependent or angiotensin II-dependent disorder in an amount effective therefore, and a pharmaceutically acceptable vehicle or diluent are also disclosed. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compound of formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. In some embodiments, the amount of the compound of formula I administered in the formulation can be 800 mg per unit dosage. In some embodiments, the amount of the compound of formula I administered per day can be about 800 mg. For example, about 400 mg of the compound can be administered in a formulation twice a day, about 200 mg of the compound in the formulation can be administered in a formulation four times a day, about 100 mg of the compound in the formulation can be administered in a formulation eight times a day.

The compound of formula I, for example, be administered in a form suitable for immediate release or extended release. Immediate release or extended release may be achieved by the use of suitable pharmaceutical compositions comprising the compound of formula I, or, particularly in the case of extended release, by the use of devices such as subcutaneous implants or osmotic pumps. In some embodiments, the amount of the compound of formula I, in the immediate release formulation, can be about 800 mg per unit dosage. In some embodiments, the amount of the compound of formula I, in the immediate release formulation, administered per day can be about 800 mg. For example, about 400 mg of the compound can be administered in an immediate release formulation twice a day, about 200 mg of the compound in an immediate release formulation can be administered four times a day, about 100 mg of the compound in an immediate release formulation can be administered eight times a day.

The compound of formula I may also be administered liposomally. For example, the active substance can be utilized in a composition such as tablet, capsule, solution or suspension containing about 5 mg to about 1000 mg per unit dosage of the compound of formula I or in topical form for wound healing (0.01 to 5% by weight the compound of formula I, 1 to 5 treatments per day). In some embodiments, the amount of the compound of formula I, administered liposomally, can be about 800 mg per unit dosage. In some embodiments, the amount of the compound of formula I, in the liposome formulation, administered per day can be about 800 mg. For example, about 400 mg of the compound can be administered in a liposome formulation twice a day, about 200 mg of the compound in a liposome formulation can be administered four times a day, about 100 mg of the compound in a liposome formulation can be administered eight times a day.

The compound of formula I may be compounded in a conventional manner with a physiologically acceptable vehicle or carrier, excipient, binder, preservative, stabilizer, flavor, etc., or with a topical carrier. In some embodiments, the amount of the compound of formula I can be about 800 mg per unit dosage. In some embodiments, the amount of the compound of formula I administered per day can be about 800 mg. For example, about 400 mg of the compound can be administered twice a day, about 200 mg of the compound can be administered four times a day, about 100 mg of the compound can be administered eight times a day.

The compound of formula I can also be formulated in compositions such as sterile solutions or suspensions for parenteral administration. About 0.1 to about 800 milligrams of the compound of formula I, typically 200 milligrams, more typically about 400 milligrams, most typically about 800 milligrams, may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained. In some embodiments, the amount of the compound of formula I, administrated parenterally, can be about 800 mg per unit dosage. In some embodiments, the amount of compound of formula I administered per day can be about 800 mg. For example, about 400 mg of the compound can be administered twice a day, about 200 mg of the compound can be administered four times a day, or about 100 mg of the compound can be administered eight times a day.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the compound of formula I with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene). For example, the compound of formula I may be administered topically to treat peripheral vascular diseases and as such may be formulated as a cream or ointment.

The compound of formula I may be employed alone or in combination with other suitable therapeutic agents useful in the treatment of endothelin-dependent or angiotensin II-dependent disorders. For example, the compound of formula I can be formulated in combination with endothelin converting enzyme (ECE) inhibitors, such as phosphoramidon; thromboxane receptor antagonists such as ifetroban; potassium channel openers; thrombin inhibitors (e.g., hirudin and the like); growth factor inhibitors such as modulators of PDGF activity; platelet activating factor (PAF) antagonists; anti-platelet agents such as GPIIb/IIIa blockers (e.g., abciximab, eptifibatide, and tirofiban), P2Y(AC) antagonists (e.g., clopidogrel, ticlopidine and CS-747), and aspirin; anticoagulants such as warfarin, low molecular weight heparins such as enoxaparin, Factor VIIa inhibitors, and Factor Xa inhibitors such as those described in U.S. Pat. No. 6,297,233, issued Oct. 2, 2001; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; vasopepsidase inhibitors (dual NEP-ACE inhibitors) such as omapatrilat and gemopatrilat; HMG CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants such as questran; niacin; anti-atherosclerotic agents such as ACAT inhibitors; MTP inhibitors such as those described in U.S. Ser. No. 09/007,938 filed Jan. 16, 1998; calcium channel blockers such as amlodipine besylate; potassium channel activators; alpha-adrenergic agents, beta-adrenergic agents such as carvedilol and metoprolol; anti-arrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase and anisoylated plasminogen streptokinase activator complex (APSAC); anti-diabetic agents such as biguanides (e.g. metformin), glucosidase inhibitors (e.g., acarbose), insulins, meglitinides (e.g., repaglinide), sulfonylureas (e.g., glimepiride, glyburide, and glipizide), biguanide/glyburide combinations such as those described in U.S. Pat. No. 6,586,438, issued Jul. 1, 2003 and U.S. Pat. No. 7,598,262, issued Oct. 6, 2009; thiozolidinediones (e.g. troglitazone, rosiglitazone and pioglitazone), and PPAR-gamma agonists; mineralocorticoid receptor antagonists such as spironolactone and eplerenone; growth hormone secretagogues such as those described in U.S. Pat. No. 6,380,184 issued Apr. 30, 2002 and U.S. Pat. No. 6,518,292 issued Feb. 11, 2003; aP2 inhibitors such as those described in U.S. Pat. No. 7,390,824 issued Jun. 24, 2008 and U.S. Ser. No. 09/390,275 filed Sep. 7, 1999; digitalis; ouabian; non-steroidal antiinflammatory drugs (NSAIDS) such as aspirin and ibuprofen; phosphodiesterase inhibitors such as PDE III inhibitors (e.g., cilostazol) and PDE V inhibitors (e.g., sildenafil); protein tyrosine kinase inhibitors; antiinflammatories; antiproliferatives such as methotrexate, FK506 (tacrolimus, Prograf), mycophenolate and mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin); cyclosporins; steroids such as prednisone or dexamethasone; gold compounds; cytotoxic drugs such as azathiprine and cyclophosphamide; TNF-alpha inhibitors such as tenidap; anti-TNF antibodies or soluble TNF receptor such as etanercept (Enbrel) rapamycin (sirolimus or Rapamune), leflunimide (Arava); and cyclooxygenase-2 (COX-2) inhibitors such as celecoxib (Celebrex) and rofecoxib (Vioxx).

If formulated as a fixed dose, such combination products employ the compound of formula I within the dosage range described below and the other pharmaceutically active agent within its approved dosage range. The compound of formula I may also be formulated with, or useful in conjunction with, antifungal and immunosuppressive agents such as amphotericin B, cyclosporins and the like to counteract the glomerular contraction and nephrotoxicity secondary to such compounds. The compound of formula I may also be used in conjunction with hemodialysis.

The above other therapeutic agents, when employed in combination with the compound of formula I, may be used, for example, in those amounts indicated in the Physicians' Desk Reference (PDR) or as otherwise determined by one of ordinary skill in the art.

The following assays may be employed in ascertaining the degree of activity of a compound ("drug") as an endothelin and angiotensin II receptor antagonist. The compound of formula I described in the following Examples has been tested in these assays, and has shown activity.

$ET_{A/B}$ Attached Cell Binding Assay

CHO-K1 cells expressing either the human endothelin A or endothelin B receptor were cultured in Ham's F12 media (Gibco/BRL, Grand Island, N.Y.) with 10% fetal bovine serum (Hyclone), supplemented with 300 μg/mL Geneticin (G-418 Gibco BRL Products, Grand Island, N.Y.) and maintained at 37° C. with 5% $CO_2$ in a humidified incubator. Twenty four hours prior to assay, the cells were treated with 0.25% trypsin-EDTA and were seeded in Falcon, 96 well tissue culture plates at a density of $1.8 \times 10^4$ cells/well (the monolayer should reach 80-90% confluency by the day of assay).

In the attached cell assay, culture media was aspirated from each well and the monolayers were washed with 50 μL of PBS (Mg$^{++}$, Ca$^{++}$ free). The binding assay was performed in a total volume of 125 μL consisting of assay buffer (50 mM Tris, pH 7.4, including 1% BSA, and 2 μM phosphoramidon), and 25 μL of either 500 nM ET-1 (to define nonspecific binding) or competing drug. The reaction was initiated with the addition of 25 μL of 0.25 nM [$^{125}$I]-ET-1 (New England Nuclear). Incubation was carried out with gentle orbital shaking, at 4° C., reaching equilibrium at 4 hours. The reaction was terminated by aspiration of the reaction buffer and two subsequent washes with cold PBS (Mg$^{++}$, Ca$^{++}$ free). The cells were dissociated by the addition of 100 μL of 0.5N NaOH followed by incubation for 40 minutes. Samples were then transferred from the 96 well format into tubes for counting in a Cobra gamma counter (Packard). Data was analyzed with curve fitting software by Sigma plot.

RASMC Binding Assay

Assays were conducted in a total volume of 250 μL in 96 well microtitre plates. The incubation mixture contained 50 μL [125]I-Sar-Ile-Angiotensin II (0.2 nM), 25 μL of drug dissolved in DMSO, or angiotensin II (1 μM) to define non-specific binding. Binding to rat aortic smooth muscle cells (RASMCs) was conducted in RPMI media (Gibco BRL Products, Grand Island, N.Y.) containing 0.1% BSA for 2 hours at room temperature with continuous shaking. Unbound radioligand was washed from the wells. The RASMCs with bound radioligand are lysed with 1% Triton X and 0.1% BSA in distilled water for 15 minutes at room temperature with continuous shaking. The solution in each well was transferred to tubes and placed in a gamma counter.

All documents cited in the present specification are incorporated herein by reference in their entirety.

The following Examples illustrate embodiments of the present disclosure, and are not intended to limit the scope of the claims. Abbreviations employed herein are defined below.

ABBREVIATIONS

Ac=acetyl
BOC=tert-butoxycarbonyl
n-Bu=n-butyl
BSA=bovine serum albumin
bp=boiling point
CDI=1,1' carbonyldiimidazole
d=days
DIBAL-H=diisobutylaluminum hydride
DMF=N,N-dimethylformamide
DMSO=dimethylsulfoxide
EDTA=ethylenediaminetetraacetic acid
eq=equivalents
Et=ethyl
ET=endothelin
ET-1=endothelin-1
EtOAc=ethyl acetate
EtOH=ethanol
g=grams
h=hours
kg=kilograms
Me=methyl
MEM=methoxyethoxymethyl
MeOH=methanol
m2/g=square meters per gram, is used as a measurement of particle surface area
min=minutes
mL=milliliters
mmol=millimoles
mm Hg=millimeters of mercury
RH=relative humidity
MOM=methoxymethyl
mp=melting point
Ms=methanesulfonyl
NBS=N-bromosuccinimide
° C.=degrees Celsius
° F.=degrees Fahrenheit
PBS=phosphate buffered saline
Ph=phenyl
n-Pr=n-propyl
μL=microliters
μg=micrograms
SEM=2-(trimethylsiloxy)ethoxymethyl
rt=room temperature
TFA=trifluoroacetic acid
THF=tetrahydrofuran

GENERAL METHODS

The following General Methods were employed in the Preparations and Examples.

General Method 1: Alkylation of Heterocycles or Aliphatic Alcohols

RCH$_2$X→RCH$_2$—OCH$_2$CH$_3$ or RCH$_2$-Heterocycle

X=Br or MsO

Sodium hydride (60% dispersion in mineral oil, 1.2 eq) was added at 0° C. to a 1.0 M solution or suspension of an appropriate heterocycle or ethyl alcohol (1.5 eq) in DMF. The mixture was allowed to warm to rt, was stirred for 20 min, and was then cooled back to 0° C. To the heterocycle mixture was added a solution of the appropriate alkyl bromide or alkyl methanesulfonate (1.0 eq) in a minimal amount of DMF. The resultant mixture was allowed to warm to rt and was stirred for 16-24 h. The reaction mixture was diluted with EtOAc and washed with water and brine. The organic layer was dried over sodium sulfate and concentrated, and the residue chromatographed on silica gel with hexanes/ethyl acetate as eluant to yield the alkylation product.

General Method 2: Reduction of an Aromatic Nitrile to an Aromatic Aldehyde Using DIBAL-H ArCN→ArCHO DIBAL-H (1.5 M solution in toluene, 1.5 eq) was added dropwise at 0° C. to a 0.5 M solution of an aromatic nitrile (1.0 eq) in toluene or 9:1 toluene/dichloromethane. The solution was stirred at 0° C. for 1-4 h, and was then treated with excess methanol. After 15 min, 2N hydrochloric acid was added and the mixture was stirred vigorously for an additional 15 min. The layers were separated, and the aqueous layer was extracted with ethyl acetate. The combined organic layers were dried over sodium sulfate and concentrated to yield the crude aldehyde, which was either carried on crude or purified via silica gel chromatography using hexanes/ethyl acetate as eluant.

General Method 3: Suzuki Coupling of Aryl Bromides with Arylboronic Acids

ArBr+Ar'B(OR)$_2$→Ar—Ar'

R=H or Alkyl

A solution of 1.0 eq of an arylboronic acid (or ester) and the appropriate aryl bromide (1.0 eq) in 2:1 toluene:ethanol (0.1 M concentration for each reagent) was sparged with nitrogen for 15 minutes. Tetrakis(triphenylphosphine)palladium (0) (0.05 eq) and 2 M aqueous sodium carbonate (3 eq) were added and the mixture was heated at 85° C. for 3 h under a nitrogen atmosphere. The mixture was cooled and ethyl acetate and water were added. The organic layer was washed once with saturated aqueous sodium carbonate, dried over sodium sulfate, and concentrated. The residue was chromatographed on silica gel using hexanes/ethyl acetate as eluant to yield the biaryl product.

Non-limiting examples of arylboronic acids used: [2-[[(4,5-dimethyl-3-isoxazolyl)][(2-methoxyethoxy)methyl]amino]-sulfonyl]phenyl]boronic acid (prepared as described in U.S. Pat. No. 5,612,359 and U.S. patent application Ser. No. 09/013,952, filed Jan. 27, 1998); 2-[[N-(4,5-dimethyl-3-isoxazolyl)-N-(methoxymethyl)amino]sulfonyl]-phenyl-boronic acid.

General Method 4: Reduction of Aryl Aldehydes to Benzylic Alcohols Using Sodium Borohydride ArCHO→ArCH$_2$—OH 

Sodium borohydride (0.5 eq) was added at 0° C. to a 0.2 M solution of an aromatic aldehyde in absolute ethanol or methanol. The mixture was allowed to warm to rt and stirred for 1-2 h. Aqueous potassium dihydrogen phosphate solution (or dilute hydrochloric acid) was added and the mixture was stirred for an additional 15 min. The mixture was partially concentrated and the residue partitioned between ethyl acetate and water. The aqueous layer was extracted twice with ethyl acetate and the combined organic extracts were dried over sodium sulfate and concentrated. The crude benzylic alcohol was either used directly or was purified by silica gel chromatography using hexanes/ethyl acetate as eluant.

General Method 5: Conversion of Benzyl Alcohols to Benzyl Bromides

RCH$_2$OH→RCH$_2$Br 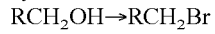

To a 0.2 M solution of the benzyl alcohol in DMF at 0° C. was added carbon tetrabromide (1.5 eq) followed by triphenylphosphine (1.5 eq). The mixture was stirred at 0° C. for 4 h, diluted with 10 parts 2:1 hexanes/ethyl acetate, and washed with water and brine. The solution was dried over sodium sulfate and concentrated, and the residue chromatographed on silica gel using hexanes/ethyl acetate as eluant to yield the benzyl bromide product.

General Method 6: Hydrolysis of SEM or MEM Sulfonamide Protecting Groups Using Hydrochloric Acid/Ethanol

R=MEM or SEM

To a 0.1 M solution of a SEM- or MEM-protected N-heteroaryl sulfonamide in one volume of 95% EtOH was added an equal volume of 6N aqueous HCl, and the resulting solution was heated at reflux for 1 h. The reaction mixture was concentrated and the pH of the solution was adjusted to pH 8 using aqueous sodium bicarbonate solution. It was then reacidified to pH 5 with glacial acetic acid. The mixture was extracted with three portions of ethyl acetate. The combined organic extracts were washed with water and brine, dried over sodium sulfate, and concentrated. The residue was purified by reverse-phase preparative HPLC, or by silica gel chromatography using chloroform/methanol or hexanes/acetone as eluant.

General Procedure: Purification by Anion Exchange Chromatography

Anion exchange chromatography was performed on Varian SAX cartridges (acetate form, 1.5-3 g) or United Chemical Technologies CUQAX13M6-AC cartridges (acetate form, 3 g). Following a methanol rinse, the cartridge was loaded with a dichloromethane solution of crude product. Elution of impurities with dichloromethane, followed by elution of the desired product with 1-3% TFA in dichloromethane or dichloromethane/methanol, provided the purified product.

General Procedure: Purification by Reverse-Phase Preparative HPLC

Reverse-phase preparative HPLC was performed with Shimadzu 8A liquid chromatographs using YMC S5 ODS columns (20×100, 20×250, or 30×250 mm). Gradient elution was performed with methanol/water mixtures in the presence of 0.1% TFA. In some cases a product eluting as a TFA salt was subsequently converted to the corresponding free base by extraction from aqueous sodium bicarbonate or sodium carbonate solution.

Analytical HPLC Methods Employed in Characterization of Examples

Analytical HPLC was performed on Shimadzu LC10AS liquid chromatographs using the following methods: A. Linear gradient of 0 to 100% solvent B over 4 min, with 1 min hold at 100% B; UV visualization at 220 nm Column: YMC S5 ODS Ballistic 4.6×50 mm Flowrate: 4 ml/min Solvent A: 0.1% trifluoroacetic acid, 90% water, 10% methanol Solvent B: 0.1% trifluoroacetic acid, 90% methanol, 10% water B. Linear gradient of 0 to 100% solvent B over 30 min, with 5 min hold at 100% B; UV visualization at 254 nm Column: YMC S3 ODS 6.times.150 mm Flowrate: 1.5 ml/min Solvent A: 0.2% phosphoric acid, 90% water, 10% methanol Solvent B: 0.2% phosphoric acid, 90% methanol, 10% water C. Linear gradient of 0 to 100% solvent B over 4 min, with 1 min hold at 100% B UV visualization at 220 nm Column: YMC S5 ODS Ballistic 4.6×50 mm Flowrate: 4 ml/min Solvent A: 0.2% phosphoric acid, 90% water, 10% methanol Solvent B: 0.2% phosphoric acid, 90% methanol, 10% water D. Linear gradient of 45 to 100% solvent B over 2 min, with 1 min hold at 100% B; UV visualization at 220 nm Column: Phenomenex Primesphere 4.6×30 mm Flowrate: 5 ml/min Solvent A: 0.2% phosphoric acid, 90% water, 10% methanol Solvent B: 0.2% phosphoric acid, 90% methanol, 10% water E. Same conditions as (B), but with a linear gradient of 40 to 100% solvent B over 30 min, with 5 min hold at 100% B F. Same conditions as (B), but with a linear gradient of 70 to 100% solvent B over 30 min, with 5 min hold at 100% B G. Same conditions as (D), but with a linear gradient of 40 to 100% solvent B over 2 min, with 1 min hold at 100% B H. Linear gradient of 0 to 100% solvent B over 2 min, with 1 min hold at 100% B; UV visualization at 220 nm Column: Phenomenex Primesphere 4.6×30 mm Flowrate: 5 ml/min Solvent A: 0.1% trifluoroacetic acid, 90% water, 10% methanol Solvent B: 0.1% trifluoroacetic acid, 90% methanol, 10% water I. Same conditions as (B), but with a linear gradient of 50 to 100% solvent B over 30 min, with 5 min hold at 100% B J. Same conditions as (C), but with a linear gradient of 0 to 100% solvent B over 8 min, with 1 min hold at 100% B K. Same conditions as (D), but with a linear gradient of 0 to 100% solvent B over 2 min, with a 1 minute hold at 100% B.

EXAMPLES

Example 1

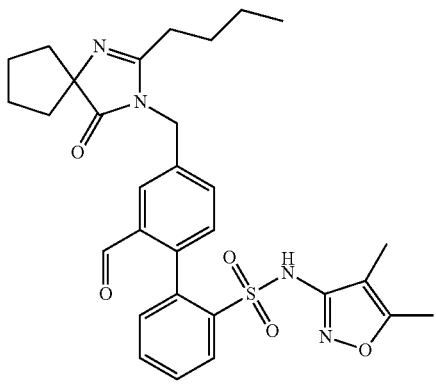 [SMILES: CCCCC1=NC2(CCCC2)C(=O)N1Cc1ccc(-c2ccccc2S(=O)(=O)Nc2noc(C)c2C)c(C=O)c1]

Name: 4'-[(2-Butyl-4-oxo-1,3-diazaspiro[4.4]non-1-en-3-yl)methyl]-2'-formyl-N-(4,5-dimethyl-3-isoxazolyl)-[[1,1'-biphenyl]-2-sulfonamide]

A. 4'-[(2-Butyl-4-oxo-1,3-diazaspiro[4.4]non-1-en-3-yl)methyl]-2'-formyl-N-(4,5-dimethyl-3-isoxazolyl)-N-(2-methoxyethoxymethyl)[1,1'-biphenyl]-2-sulfonamide Palladium catalyzed Suzuki coupling of 4-bromo-3-(ethoxymethyl)benzaldehyde and [2-[[(4,5-dimethyl-3-isoxazolyl)[(2-methoxyethoxy)methyl]amino]sulfonyl]phenyl] boronic acid was performed according to General Method 3 to afford N-(4,5-dimethyl-3-isoxazolyl)-4'-(ethoxycarbonyl)-T-(formye-N-((methoxyethoxy)methyl) [1,1'-biphenyl]-2-sulfonamide (81%) following silica-gel chromatography.

B. 4'-[(2-Butyl-4-oxo-1,3-diazaspiro[4.4]non-1-en-3-yl)methyl]-2'-formyl-N-(4,5-dimethyl-3-isoxazolyl)-[1,1'-biphenyl]-2-sulfonamide Treatment of N-(4,5-dimethyl-3-isoxazolyl)-4'-(ethoxycarbonyl)-2'-(formyl)-N-((methoxyethoxy)methyl) [1,1'-biphenyl]-2-sulfonamide with 6N aqueous hydrochloric acid according to General Method 6 to remove the MEM protecting group provided the title compound (85%): Rf=0.38, 5% MeOH in methylene chloride.

Example 2

4'-[(2-Butyl-4-oxo-1,3-diazaspiro[4.4]non-1-en-3-yl)methyl]-N-(4,5-dimethyl-3-isoxazolyl)-2'-(ethoxymethyl)-[1,1'-biphenyl]-2-sulfonamide was synthesized by combinations of the General Methods.

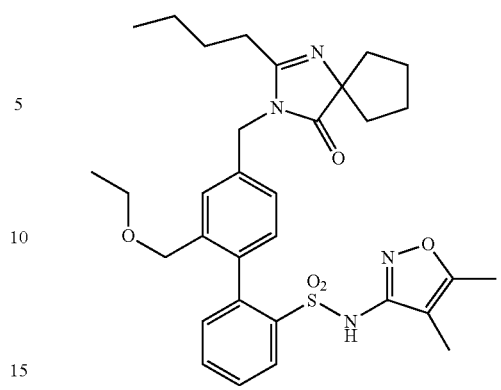

Name: 4'-[(2-Butyl-4-oxo-1,3-diazaspiro[4.4]non-1-en-3-yl)methyl]-N-(4,5-dimethyl-3-isoxazolyl)-2'-(ethoxymethyl)-[1,1'-biphenyl]-2-sulfonamide

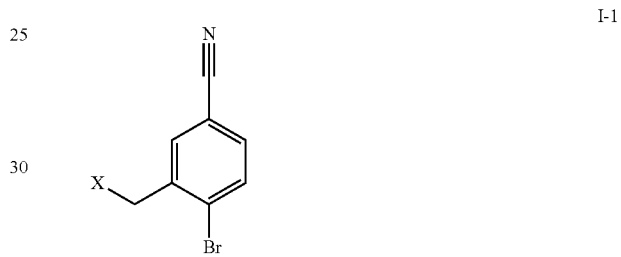

I-1

Starting Material: X—Br or OMs
General Methods Applied (yield, %): General Method 1, EtOH (77); General Method 2 (80); General Method 3 (70); General Method 4 (98); General Method 5 (80); General Method 1 (83); General Method 6 (86)
M/z (MH)$^+$: 593
HPLC % Purity: >98
HPLC retention time, min (HPLC method): 18.75 (E)

Example 3

4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide [crystalline]

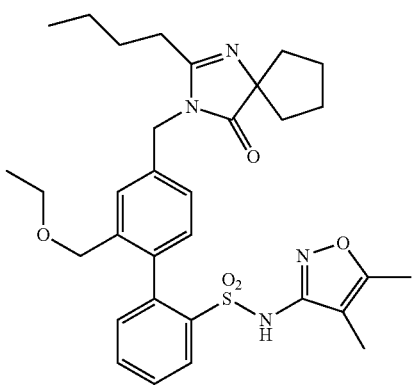 [SMILES: CCCCC1=NC2(CCCC2)C(=O)N1Cc1ccc(-c2ccccc2S(=O)(=O)Nc2noc(C)c2C)c(COCC)c1]

Alternative Synthesis of 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide Step A. Ethyl 4-bromo-3-(bromomethyl)benzoate Ethyl 4-bromo-3-methylbenzoate (110 g, 450 mmol.) was treated with NBS according to the procedure of Example 5. Silica gel chromatography with hexanes/ethyl acetate as eluant provided ethyl 4-bromo-3-(bromomethyl)benzoate (91 g, 62%) as a white solid.

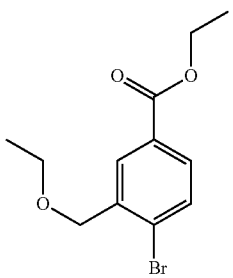 [SMILES: CCOCc1cc(C(=O)OCC)ccc1Br]

Step B. Ethyl 4-bromo-3-(ethoxymethyl)benzoate

A solution of ethyl 4-bromo-3-(bromomethyl)benzoate (89 g, 280 mmol.) in a mixture of ethanol (300 mL) and DMF (50 mL) was treated at 0° C. with sodium ethoxide (135 mL of a 21% solution in ethanol). The mixture was allowed to warm to rt and was stirred for 16 h. The ethanol was evaporated under reduced pressure. Ethyl acetate was added to the residue and the mixture was washed with water and brine. The organic layer was dried over sodium sulfate and concentrated, and the residue was chromatographed on silica gel using hexanes/ethyl acetate as eluant to provide Ethyl 4-bromo-3-(ethoxymethyl)benzoate (67 g, 84%) as a slightly yellow oil.

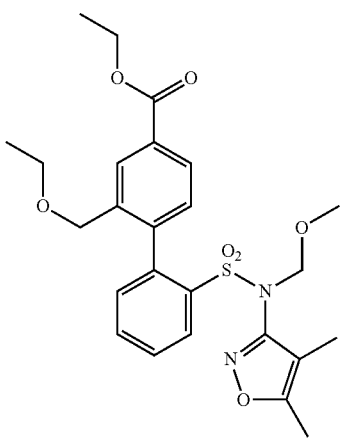 [SMILES: CCOCc1cc(C(=O)OCC)ccc1-c1ccccc1S(=O)(=O)N(COC)c1noc(C)c1C]

Step C. N-(4,5-Dimethyl-3-isoxazolyl)-4'-(ethoxycarbonyl)-2'-(ethoxymethyl)-N-(methoxymethyl) [1,1'-biphenyl]-2-sulfonamide Ethyl 4-bromo-3-(ethoxymethyl)benzoate (32 g, 100 mmol) was subjected to Suzuki coupling with 2[[N-(4,5-dimethyl-3-isoxazolyl)-N-(methoxymethyl)amino]sulfonyl]-phenylboronic acid according to General Method 3. Silica gel chromatography using hexanes/ethyl acetate as eluant provided N-(4,5-Dimethyl-3-isoxazolyl)-4'-(ethoxycarbonyl)-2'-(ethoxymethyl)-N-(methoxymethyl) [1,1'-biphenyl]-2-sulfonamide (52 g) as a yellow oil, contaminated with by-products deriving from the boronic acid.

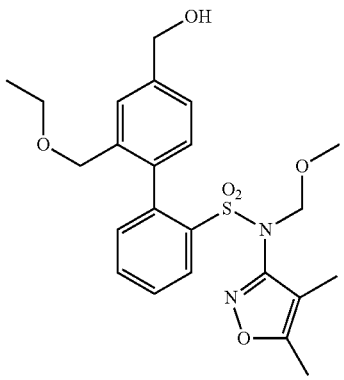 [SMILES: CCOCc1cc(CO)ccc1-c1ccccc1S(=O)(=O)N(COC)c1noc(C)c1C]

Step D. N-(4,5-Dimethyl-3-isoxazolyl)-2'-(ethoxymethyl)-4'-(hydroxymethyl)-N-(methoxymethyl) [1,1'-biphenyl]-2-sulfonamide N-(4,5-Dimethyl-3-isoxazolyl)-4'-(ethoxycarbonyl)-2'-(ethoxymethyl)-N-(methoxymethyl) [1,1'-biphenyl]-2-sulfonamide (entire sample) was treated with DIBAL-H according to the following procedure:

A solution of N-(4,5-Dimethyl-3-isoxazolyl)-4'-(ethoxycarbonyl)-2'-(ethoxymethyl)-N-(methoxymethyl) [1,1'-biphenyl]-2-sulfonamide (0.3 mmol.) in THF (5 mL) is treated with DIBAL-H (0.53 mL of a 1.5 M solution in toluene, 0.8 mmol.) at −78° C. The temperature was allowed to rise to −25° C. and the mixture is stirred for 2 h. Saturated aqueous ammonium chloride is added to the cooled reaction mixture, followed by extraction with ethyl acetate. The combined organic layers are dried over sodium sulfate and concentrated to provide N-(4,5-Dimethyl-3-isoxazolyl)-2'-(ethoxymethyl)-4'-(hydroxymethyl)-N-(methoxymethyl) [1,1'-biphenyl]-2-sulfonamide as a crude yellow oil.

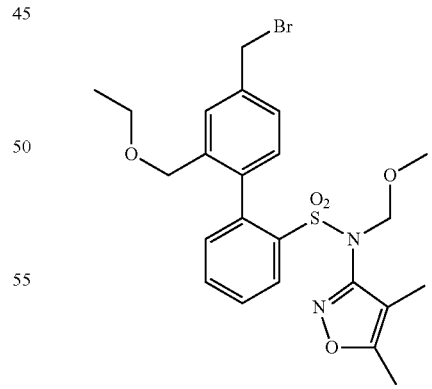

Step E. 4'-(Bromomethyl)-N-(4,5-dimethyl-3-isoxazolyl)-2'-(ethoxymethyl)-N-(methoxymethyl) [1,1'-biphenyl]-2-sulfonamide N-(4,5-Dimethyl-3-isoxazolyl)-T-(ethoxymethyl)-4'-(hydroxymethyl)-N-(meth oxymethyl) [1,1'-biphenyl]-2-sulfonamide (entire sample) was converted to the corresponding bromide according to General Method 5. Silica gel chromatography using hexanes/ethyl acetate as eluant provided 4'-(Bromomethyl)-N-(4,5-dimethyl-3-isoxazolyl)-T-(ethoxymethyl)-N-(methoxymethyl) [1,1'-biphenyl]-2-sulfonamide (38 g, purity estimated to be 83% by $^1$H NMR) as a light yellow oil.

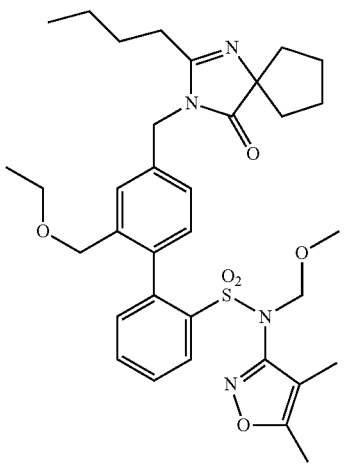 [SMILES: CCCCC1=NC2(CCCC2)C(=O)N1Cc1ccc(-c2ccccc2S(=O)(=O)N(COC)c2noc(C)c2C)c(COCC)c1]

Step F. 4'-[(2-Butyl-4-oxo-1,3-diazaspiro[4.4]non-1-en-3-yl)methyl]-N-(4,5-dimethyl-3-isoxazolyl)-2'-(ethoxymethyl)-N-(methoxymethyl) [1,1'-biphenyl]-2-sulfonamide 4'-(Bromomethyl)-N-(4,5-dimethyl-3-isoxazolyl)-2'-(ethoxymethyl)-N-(methoxymethyl) [1,1'-biphenyl]-2-sulfonamide (entire sample) was used to alkylate 2-butyl-1,3-diazaspiro[4.4]non-1-en-4-one according to General. Method 1. The crude residue was chromatographed on silica gel using hexanes/ethyl acetate/triethylamine as eluant to provide 4'-[(2-Butyl-4-oxo-1,3-diazaspiro[4.4]non-1-en-3-yl)methyl-N-](4,5-dimethyl-3-isoxazolyl)-2'-(ethoxymethyl)-N-(methoxymethyl) [1,1'-biphenyl]-2-sulfonamide (32 g, 53% from Step B) as a slightly yellow oil.

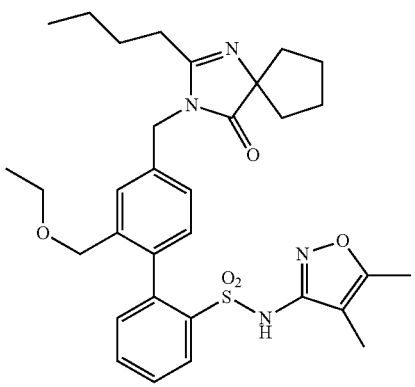 [SMILES: CCCCC1=NC2(CCCC2)C(=O)N1Cc1ccc(-c2ccccc2S(=O)(=O)Nc2noc(C)c2C)c(COCC)c1]

Step G. 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide The MOM protecting group of 4'-[(2-Butyl-4-oxo-1,3-diazaspiro[4.4]non-1-en-3-yl)methyl]-N-(4,5-dimethyl-3-isoxazolyl)-2'-(ethoxymethyl)-N-(methoxymethyl) [1,1'-biphenyl]-2-sulfonamide (32 g, 53 mmol.) was removed according to General Method 6. The crude product was purified by silica gel chromatography using hexanes/ethyl acetate/acetic acid as eluant to provide the title compound (26 g, 88%) as an amorphous foam: MS n/e 593 (ESI+ mode); HPLC retention time 18.75 min (HPLC method E); HPLC purity>96%.

Example 4

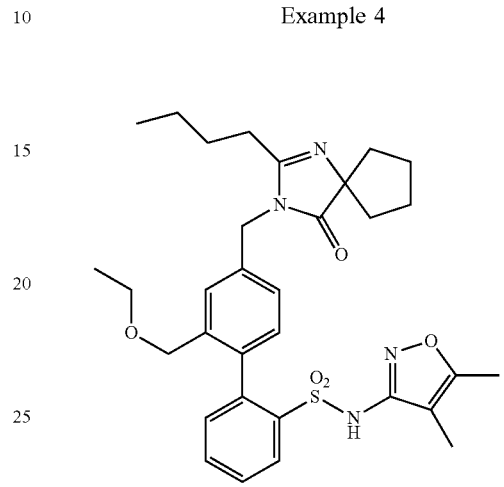

Step H. 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide Crystallization The amorphous 4'-[(2-Butyl-4-oxo-1,3-diazaspiro[4.4]non-1-en-3-yl)methyl]-N-(4,5-dimethyl-3-isoxazolyl)-2'-(ethoxymethyl) [1,1'-biphenyl]-2-sulfonamide (1 g) was dissolved in 5 mL of isopropanol then 5 mL of water was added to the mixture dropwise and the mixture was warmed up to 40° C. to provide a clear solution. The solution was allowed to stand at room temperature and the white crystals thus obtained were filtered and washed with a small amount of 2:1 mixture of isopropanol/water and dried to give 0.87 g of a white crystalline solid. mp: 148° C.

Example 5

General Method 1: Benzylic Bromination Using N-Bromosuccinimide

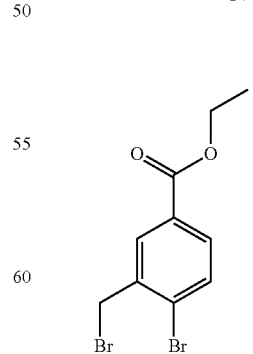

To a 0.4 M solution of a methyl-substituted aromatic compound, such as ethyl 4-bromo-3-methylbenzoate, in carbon tetrachloride was added N-bromosuccinimide (1.05 eq) and benzoyl peroxide (0.03 eq), and the mixture was heated at reflux for 8-16 h. The mixture was cooled and filtered and the filtrate concentrated. The residue was purified by trituration with 3:1 hexanes/ethyl acetate, or by silica gel chromatography using hexanes/ethyl acetate as eluant to provide the mono-brominated product, such as ethyl 4-bromo-3-(bromomethyl)benzoate.

Example 6

200 mg and 400 mg Strength Tablets for Oral Administration Using Low Shear Granulation Two formulations utilizing microcrystalline cellulose versus a mixture of microcrystalline cellulose and lactose were processed using low shear granulation. The compositions of Formulation B and Formulation C are shown in Tables 1 and 2. 200 mg and 400 mg strength tablets were made using a low shear wet granulation method of manufacture with a 57% drug load.

TABLE 1

Compositions of 200 mg Strength Tablets

| INGREDIENT | Formulation C | | Formulation B | |
|---|---|---|---|---|
| | Amount mg/tablet | Composition % by weight | Amount mg/tablet | Composition % by weight |
| Intragranular | | | | |
| Compound of formula I (API) | 200.0 | 57.1 | 200.0 | 57.1 |
| Microcrystalline Cellulose, NF Avicel PH 101 | 102.4 | 29.3 | 76.43 | 21.8 |
| Lactose Monohydrate 316 (Fast Flow) | — | — | 38.22 | 10.9 |
| Sodium Lauryl Sulfate, NF | — | — | 3.50 | 1.0 |
| Croscarmellose Sodium (Ac-Di-Sol) | 8.75 | 2.5 | 8.75 | 2.5 |
| Hydroxypropyl-cellulose, EXF | 10.5 | 3.0 | 10.5 | 3.0 |
| Poloxamer 188, NF | 17.5 | 5.0 | — | — |
| Extragranular | | | | |
| Croscarmellose Sodium (Ac-Di-Sol) | 8.75 | 2.5 | 8.75 | 2.5 |
| Colloidal Silicone Dioxide, NF (Cab-O-Sil M5P) | 0.35 | 0.1 | 0.35 | 0.1 |
| Magnesium Stearate, NF (Vegetable Grade) | 1.75 | 0.5 | 3.50 | 1.0 |
| Total | 350 | | 350 | |

TABLE 2

Compositions of 400 mg Strength Tablets

| Ingredient | Formulation C | | Formulation B | |
|---|---|---|---|---|
| | Amount mg/tablet | Composition % by weight | Amount mg/tablet | Composition % by weight |
| Intragranular | | | | |
| Compound of formula I (API) | 400.0 | 57.1 | 400.0 | 57.1 |
| Microcrystalline Cellulose, NF Avicel PH 101 | 204.8 | 29.3 | 152.86 | 27.8 |
| Lactose Monohydrate 316 (Fast Flow) | — | — | 76.44 | 10.9 |
| Sodium Lauryl Sulfate, NF | — | — | 7.0 | 1.0 |
| Croscarmellose Sodium (Ac-Di-Sol) | 17.5 | 2.5 | 17.5 | 2.5 |
| Hydroxypropyl-cellulose, EXF | 21.0 | 3.0 | 21.0 | 3.0 |
| Poloxamer 188, NF | 35.0 | 5.0 | — | — |
| Extragranular | | | | |
| Croscarmellose Sodium (Ac-Di-Sol) | 17.5 | 2.5 | 17.5 | 2.5 |
| Colloidal Silicone Dioxide, NF (Cab-O-Sil M5P) | 0.7 | 0.1 | 0.7 | 0.1 |
| Magnesium Stearate, NF (Vegetable Grade) | 3.5 | 0.5 | 7.0 | 1.0 |
| Total | 700 | | 700 | |

The formulations were granulated with a Kitchen Aid planetary type mixer using milli-Q water as the granulation liquid. Formulation C was granulated with a total of 84 grams of water at an addition rate of 14 grams per minute. Formulation B was granulated with a total of 94 grams of water with an addition rate of 14 grams per minute. Both granulations were tray dried in a 60° C. vented oven for approximately 15 hours. The dried granulations were milled using a 197S Quadro Comil equipped with a 050G grater screen, a round impeller, and a 0.175" spacer at 20% Comil speed. The extragranular excipients were adjusted based on the percent yield. Each formulation was bag blended for 5 minutes before the lubrication was added and blended an additional 1 minute after the lubrication was added.

Physical properties of the blends were determined (bulk density and LOD moisture content). The blend was compressed on a Piccola BD tablet press set up with a gravity feed frame and hopper at a speed of 36 rpm. Pre-compression, main compression and ejection forces were monitored using "The Director" software, written by SMI Inc. Tablet weights of 350 mg and 700 mg were targeted to produce 200 and 400 mg strength tablets respectively from each formulation. The 350 mg tablets (200 mg strength) were compressed with 0.2500"×0.5000" capsule shaped standard concave tooling and the 700 mg tablets (400 mg strength) were compressed with 0.3300×0.7100 oval standard concave tooling. A range of tablet hardnesses were targeted to determine the robustness of the formulations and tablet thickness was recorded. Tablet weight, hardness, thickness and friability were monitored in-process.

The low shear granulation process succeeded in moderately densifying the formulations and tray drying brought the wet granulation to an acceptably low moisture content as indicated by the density and LOD results as shown in Table 3.

TABLE 3

Bulk Density and LOD Results for Formulation C and Formulation B

| Formulation | Bulk density of granulation (g/ml) | LOD of wet granulation (%) | LOD after tray drying (%) |
|---|---|---|---|
| Formulation C | 0.39 | 23.61 | 1.10 |
| Formulation B | 0.40 | 26.90 | 1.39 |

Both tablet strengths of Formulation C and Formulation B performed well on the rotary tablet press with regard to flow and compressibility resulting in stable tablet weights and acceptable tablet hardness and low friability (Tables 4 and 5). Both tablet formulations disintegrated rapidly in 0.1 N HCl, but the Formulation B disintegrated faster than Formulation C (Table 5). Formulation C experienced tablet sticking issues during the compression trials. Further, addition of magnesium stearate was studied.

TABLE 4

Tablet Physical Testing for Formulation C and Formulation B

| Formulation | Average tablet weight (mg) [n = 10] | Average tablet thickness (in) [n = 10] | Average tablet hardness (kp) [n = 10] |
|---|---|---|---|
| Formulation C 200 mg strength tablets | 351.5 | 0.196 | 13.8 |
| Formulation C 400 mg strength tablets | 697.6 | 0.269 | 12.1 |
| Formulation B 200 mg strength tablets | 348.0 | 0.202 | 12.7 |
| Formulation B 400 mg strength tablets | 716.7 | 0.287 | 9.6 |

TABLE 5

Disintegration Results for 200 mg and 400 mg Strength Tablets for Formulation C and Formulation B

| | Target Hardness (kp) | Disintegration (0.1N HCl) Initial (min) | Disintegration (0.1N HCl) Final (min) | Friability (%) (100 Drops) [n = 10] |
|---|---|---|---|---|
| Formulation 200 mg Strength | | | | |
| Formulation C | 8-9 | 3.15 | 4.35 | 0.04 |
| Formulation B | 8-9 | 1.32 | 1.78 | 0.12 |
| Formulation C | 15 | 6.93 | 9.70 | No data |
| Formulation B | 15 | 2.57 | 4.95 | No data |
| Formulation 400 mg Strength | | | | |
| Formulation C | 8-9 | No data | No data | 0.10 |
| Formulation B | 8-9 | No data | No data | 0.20 |

HPLC-backend analysis was performed on the dissolution samples. Dissolution test results indicated that Formulation C had a substantially faster dissolution rate than Formulation B in the 0.1 N HCl dissolution media at both 50 and 60 rpm paddle speed (Table 6).

TABLE 6

Dissolution Results in 0.1N HCL Dissolution Media for 400 mg Strength Tablets: Formulation C and Formulation B

| 400 mg strength high hardness | % Dissolved vs Time (min) | | | | | |
|---|---|---|---|---|---|---|
| (~14 kp) tablet sample | 0 | 10 | 20 | 30 | 45 | 60 |
| Formulation B, 50 rpm | 0 | 37 | 53 | 61 | 67 | 71 |
| Formulation B, 60 rpm | 0 | 44 | 65 | 75 | 83 | 87 |
| Formulation C, 50 rpm | 0 | 56 | 73 | 79 | 84 | 87 |
| Formulation C, 60 rpm | 0 | 62 | 82 | 87 | 91 | 94 |

Assay and related substance results for Formulation C and Formulation B are shown in Table 7.

TABLE 7

Assay and Related Substances Results for Formulation C and Formulation B Tablets

| Sample tablet | Assay potency % label claim | % Impurity versus Relative retention time | | | | | | | Total impurities |
|---|---|---|---|---|---|---|---|---|---|
| | | RRT 0.85 | RRT 0.88 | RRT 0.96 | RRT 0.98 | RRT 1.02 | RRT 1.03 | RRT 1.21 | |
| Formulation C | 99.5 | 0.06 | 0.13 | 0.05 | 0.06 | 0.07 | 0.05 | 0.37 | 0.75 |
| Formulation B | 99.4 | 0.06 | 0.13 | 0.05 | 0.06 | 0.07 | 0.05 | 0.38 | 0.77 |

Example 7

200 mg and 400 mg Strength Tablets for Oral Administration Using High Shear Wet Granulation In Example 6, Formulation C of a microcrystalline cellulose based composition including Poloxamer 188 was observed to have a substantially faster drug release profile compared to Formulation B of a microcrystalline cellulose/lactose combination formulation (Table 6). Formulation C needed an increase in lubricant due to sticking issues seen in compression trials. In this example, the amount of magnesium stearate was increased in Formulation C to provide Formulation D. Also, a new experimental design was created to evaluate the super disintegrant sodium starch glycolate in addition to croscarmellose sodium to provide Formulation E thereby further increasing disintegration/dissolution rates. A high shear wet granulation was substituted for the low shear granulation to improve the dissolution rate and provide a manufacturing method more modern and suitable for future scale up manufacture.

Formulation D is a microcrystalline cellulose based formulation with Poloxamer 188 including a 0.5% increase in lubrication and addition of croscarmellose sodium. Formulation E is a similar formulation using sodium starch glycolate instead of croscarmellose sodium disintegrant. Formulation A is an additional formulation including microcrystalline cellulose, croscarmellose sodium with sodium lauryl sulfate in place of Poloxamer 188. Compositions of Formulations D, E, and A are shown in Tables 8 and 9. Dose proportional 200 mg and 400 mg strength tablets were prepared with the ingredients in the amount as shown in Tables 8 and 9.

The formulations were granulated using the high shear wet granulation in the 10 liter Niro PP 1 high shear granulator equipped with a 7.5 liter insert. Milli-Q water was used as the binder solution. The batch size for each formulation was 750 grams. The intra-granular materials were mixed in the granulator for 3 minutes at 300 rpm impeller speed prior to granulation. Formulation D granulation required 251 grams of water at a spray rate of 41.8 g/minute. Formulation A granulation required 322 grams of water at a spray rate of 41.8 g/minute. Formulation E required 311 grams of water at a spray rate of 52 g/minute. The impeller speed was set at 305 rpm and chopper set on high speed during granulation. The granulation end point was qualitatively determined by the "snowball" method (first test) and the granulations were mixed an additional 5 minutes at 300 rpm with no chopper. Each formulation was dried with the Niro Aeromatic MP-1 fluid bed dryer at an inlet air temperature of 65° C. to an LOD moisture content of less than 2.0%. The dried granulations were milled using a 197S Quadro Comil equipped with a 0.050" grater screen, a round impeller and a 0.175" spacer at 20% Comil speed.

TABLE 8

Compositions of 200 mg Strength Tablets for Formulation D, Formulation A and Formulation E

| Ingredient | Formulation D | | Formulation A | | Formulation E | |
|---|---|---|---|---|---|---|
| | Amount mg/tablet | Composition % by weight | Amount mg/tablet | Composition % by weight | Amount mg/tablet | Composition % by weight |
| Intragranular | | | | | | |
| Compound of formula I | 200.0 | 57.1 | 200.0 | 57.1 | 200.0 | 57.1 |
| Microcrystalline Cellulose, NF Avicel PH 101 | 100.65 | 28.8 | 114.65 | 32.8 | 100.65 | 28.8 |
| Sodium Lauryl Sulfate, NF | — | — | 3.50 | 1.0 | — | — |
| Croscarmellose Sodium (Ac-Di-Sol) | 8.75 | 2.5 | 8.75 | 2.5 | — | — |
| Hydroxypropylcellulose, EXF | 10.50 | 3.0 | 10.50 | 3.0 | 10.50 | 3.0 |
| Poloxamer 188, NF | 17.5 | 5.0 | — | — | 17.5 | 5.0 |
| Sodium Starch Glycolate (EXPLOTAB ©) | — | — | — | — | 8.75 | 2.5 |
| Extragranular | | | | | | |
| Sodium Starch Glycolate (EXPLOTAB ©) | — | — | — | — | 8.75 | 2.5 |
| Croscarmellose Sodium (Ac-Di-Sol) | 8.75 | 2.5 | 8.75 | 2.5 | — | — |
| Colloidal Silicone Dioxide, NF (Cab-O-Sil M5P) | 0.35 | 0.1 | 0.35 | 0.1 | 0.35 | 0.1 |
| Magnesium Stearate, NF (Vegetable Grade) | 3.50 | 1.0 | 3.50 | 1.0 | 3.50 | 1.0 |
| Total | 350 | | 350 | | 350 | |

TABLE 9

Compositions of 400 mg Strength Tablets for Formulation D, Formulation A, and Formulation E

| Ingredient | Formulation D Amount mg/tablet | Formulation D Composition % by weight | Formulation A Amount mg/tablet | Formulation A Composition % by weight | Formulation E Amount mg/tablet | Formulation E Composition % by weight |
|---|---|---|---|---|---|---|
| Intragranular | | | | | | |
| Compound of formula I | 401.8 | 57.4 | 401.8 | 57.4 | 401.8 | 57.4 |
| Microcrystalline Cellulose, NF Avicel PH 101 | 201.3 | 28.8 | 229.3 | 32.8 | 201.3 | 28.8 |
| Sodium Lauryl Sulfate, NF | — | — | 3.50 | 1.0 | — | — |
| Croscarmellose Sodium (Ac-Di-Sol) | 17.5 | 2.5 | 17.5 | 2.5 | — | — |
| Hydroxypropylcellulose, EXF | 21.0 | 3.0 | 21.0 | 3.0 | 21.0 | 3.0 |
| Poloxamer 188, NF | 35.0 | 5.0 | — | — | 35.0 | 5.0 |
| Sodium Starch Glycolate (EXPLOTAB ©) | — | — | — | — | 17.5 | 2.5 |
| Extragranular | | | | | | |
| Sodium Starch Glycolate (EXPLOTAB ©) | — | — | — | — | 17.5 | 2.5 |
| Croscarmellose Sodium (Ac-Di-Sol) | 17.5 | 2.5 | 17.5 | 2.5 | — | — |
| Colloidal Silicone Dioxide, NF (Cab-O-Sil M5P) | 0.7 | 0.1 | 0.7 | 0.1 | 0.7 | 0.1 |
| Magnesium Stearate, NF (Vegetable Grade) | 7.0 | 1.0 | 7.0 | 1.0 | 7.0 | 1.0 |
| Total | 700 | | 700 | | 700 | |

The extragranular excipients were adjusted per the yield and added to each example granulation. The mixture was bag blend for 5 minutes. Magnesium stearate was layered into the mixture and the mixture was blended for an additional 3 minutes. The final blends were compressed on a Piccola ED tablet press using the paddle feeder feed frame at a press speed of 36 rpm. The 350 mg tablets (200 mg strength) were compressed with 0.2500"×0.5000" capsule standard concave tooling and the 700 mg tablets (400 mg strength) were compressed with 0.3300×0.7100 oval standard concave tooling. A tablet hardness of 15 KP was targeted for the formulations.

The physical properties of the final blends for Formulation D, and Formulation A, showed little difference in relation to bulk density, tap density, angle of repose, compressibility or particle size distribution (Tables 10 and 11). All examples exhibited acceptable flow as indicated by the angle of repose, compressibility and Flodex values (Table 10). All formulations exhibited low moisture as shown in Table 11. Formulation E was substantially denser than the other two Formulations and was substantially larger in its particle size distribution as shown in Table 11. The Formulation E wet granulation process produced large, well defined granules. Large hard granules produced during granulation resulted in significantly longer milling times than seen in the other examples. Some dried spheres, granules and particles could not be milled and were discarded.

TABLE 10

Bulk Density and Tap Density Results

| Formula | Bulk Density (g/ml) | Tap Density (g/ml) | Angle of Repose (°) | Flodex Orifice (mm) | Compressibility (%) |
|---|---|---|---|---|---|
| Formulation D | 0.47 | 0.61 | 29.7 | — | 16.6 |
| Formulation A | 0.48 | 0.60 | 30.1 | — | 16.6 |
| Formulation E | 0.52 | 0.64 | 29.4 | 8 | 16.7 |
| Formulation G | 0.57 | 0.67 | 31.8 | 5 | 14.3 |
| Formulation F | 0.49 | 0.63 | 32.7 | 7 | 16.7 |
| Formulation D (larger API particle size) | 0.45 | 0.56 | 34.6 | — | 16.7 |

TABLE 11

Particle Size Data of Final Blends

| Micron | Sieve | Formulation D | Formulation A | Formulation E | Formulation G | Formulation F | Formulation D (larger API particle size) 100 mg and 400 mg |
|---|---|---|---|---|---|---|---|
| 850 | 20 | 2.1 | 2.0 | 11.3 | 6.1 | 2.9 | 3.9 |
| 425 | 40 | 13.5 | 13.1 | 54.6 | 31.3 | 15.3 | 13.9 |
| 250 | 60 | 10.4 | 12.1 | 13.4 | 32.3 | 10.6 | 6.9 |

TABLE 11-continued

Particle Size Data of Final Blends

| Micron | Sieve | Formulation D | Formulation A | Formulation E | Formulation G | Formulation F | Formulation D (larger API particle size) 100 mg and 400 mg |
|---|---|---|---|---|---|---|---|
| 180 | 80 | 7.3 | 9.1 | 4.1 | 12.1 | 6.7 | 5.9 |
| 106 | 140 | 10.4 | 12.1 | 4.1 | 7.1 | 9.6 | 17.8 |
| 45 | 325 | 44.8 | 33.3 | 7.2 | 6.1 | 37.5 | 43.6 |
| <45 | Pan | 11.5 | 18.2 | 5.2 | 5.0 | 17.3 | 7.9 |

LOD results for Formulations A, D, E, G and F are shown in Table 12.

TABLE 12

LOD Results

| Formulation | LOD after Fluid Bed Drying (%) |
|---|---|
| Pre-Granulation | 1.90 |
| Formulation D | 1.50 |
| Formulation A | 1.20 |
| Formulation E | 1.00 |
| Formulation G | 0.75 |
| Formulation F | 1.00 |

All the formulation blends performed well on the tablet press (Table 13) and produced high quality, consistent, hard tablets with low friability. The increased lubricant in Formulation D eliminated the tablet sticking issues that were seen earlier in Formulation C. The tablet disintegration time at 49.70 minutes for Formulation E was significantly longer than the tablet disintegration time seen in the other examples (Table 14).

TABLE 13

Tablet Physical Testing Data for 200 mg and 400 mg Strength Tablets

| Formulation | Average Tablet Weight (mg) [n = 10] | Average Tablet Thickness (in) [n = 10] | Average Tablet Hardness (kp) [n = 10] | Tablet Friability (100 drops) (%) [n = 10] | Average Pre-Compression Force (N) | Average Compression Force (KN) | Average Ejection Force (N) |
|---|---|---|---|---|---|---|---|
| Formulation D 200 mg | 350.1 | 0.192 | 14.6 | 0.1 | 22.9 | 7.0 | 123 |
| Formulation D 400 mg | 700.6 | 0.254 | 15.0 | 0.1 | 22.9 | 8.5 | 130 |
| Formulation A 200 mg | 358.1 | 0.199 | 15.2 | 0.1 | 24.1 | 6.7 | 147 |
| Formulation A 400 mg | 704.8 | 0.264 | 14.9 | 0.2 | 20.1 | 8.0 | 160 |
| Formulation E 200 mg | 352 | 0.190 | 14.3 | 0.0 | 24.0 | 8.7 | 149.9 |
| Formulation E 400 mg | 729 | 0.258 | 15.8 | 0.1 | | 8.4 | |
| Formulation G 200 mg | 358.7 | 0.188 | 12.0 | 0.1 | 25.9 | 14.7 | 188.9 |
| Formulation G 400 mg | 707.9 | 0.245 | 11.3 | 0.3 | | | |
| Formulation F 200 mg | 350.9 | 0.191 | 14.0 | 0.0 | 27.3 | 7.7 | 169.0 |
| Formulation D (larger API particle size) 100 mg | 175.5 | 0.189 | 10.1 | 0.2 | | | |
| Formulation D (larger API particle size) 400 mg | 704.4 | 0.267 | 16.1 | 0.0 | | | |

TABLE 14

Disintegration Results for 200 mg Strength Tablets

| Formulation 200 mg Strength | Target Hardness (kp) | Disintegration (0.1N HCl) Initial (min) | Disintegration (0.1N HCl) Final (min) |
|---|---|---|---|
| Formulation D LS | 8-9 | 3.15 | 4.35 |
| Formulation B LS | 8-9 | 1.32 | 1.78 |
| Formulation D LS | 15 | 6.93 | 9.70 |
| Formulation B LS | 15 | 2.57 | 4.95 |
| Formulation A HS | 15 | 0.93 | 1.17 |
| Formulation D HS | 15 | 15.13 | 17.0 |
| Formulation E HS | 15 | 41.48 | 49.70 |
| Formulation G HS | 12 | 30.25 | 34.35 |
| Formulation F HS | 14 | 11.57 | 15.00 |

LS = low shear granulation process;
HS = high shear granulation process.

The Poloxamer 188 surfactant (Formulation D) outperformed the sodium lauryl sulfate surfactant (Formulation A) with respect to dissolution. Both Formulation A and Formulation D outperformed Formulation E. The dissolution profile for the 400 mg strength tablet, Formulation A showed a 77% drug release in 30 minutes and an 89% drug release in 60 minutes while the dissolution profile for the 400 mg strength tablet of Formulation D, showed a 92% drug release in 30 minutes and a 96% drug release in 60 minutes (Table 15).

TABLE 15

Dissolution Results for 400 mg Strength Tablets Formulation A, D and E in 0.1N HCl at 60 rpm

| 400 mg High Hardness | % Dissolved vs Time (min) | | | | | | |
|---|---|---|---|---|---|---|---|
| (~14 kp) Tablets sample | 0 | 10 | 20 | 30 | 45 | 60 | 75 |
| Formulation A | 0 | 52 | 70 | 77 | 84 | 89 | 93 |
| Formulation D | 0 | 51 | 86 | 92 | 94 | 96 | 98 |
| Formulation E | 0 | 14 | 27 | 38 | 53 | 64 | 80 |

The 200 mg strength Formulation A tablets had a faster dissolution release than the 400 mg strength tablets as shown in Table 16.

TABLE 16

Dissolution Results for Formulation A 400 mg and 200 mg Strength Tablets

| Tablets Sample | % Dissolved vs Time (min) | | | | | | |
|---|---|---|---|---|---|---|---|
| | 0 | 10 | 20 | 30 | 45 | 60 | 75 |
| Formulation A 400 mg strength tablets | 0 | 52 | 70 | 77 | 84 | 89 | 93 |
| Formulation A 200 mg strength tablets | 0 | 67 | 83 | 90 | 95 | 96 | 99 |

Both Formulation D and Formulation A were shown to have a high degree of potency with low related substances. A short term stability evaluation was performed on the 200 mg strength Formulation D and Formulation A tablets in packaged and open container conditions. The packaged tablets were placed in HDPE bottles with induction sealed closures and subjected to accelerated stability conditions at 50° C. (ambient humidity). The open container tablets were place in open bottles at 40° C./75% RH (relative humidity). The tablets were assayed at 2 and 4 week's time. The short term stability study indicated that both Formulation D and Formulation A were chemically stable formulations. 200 mg strength tablets for both Formulation D and Formulation A remained potent and with no significant increase in related substances for at least 4 weeks at 40° C./75% RH in open containers. The 50° C. closed container tablets were stable for 4 weeks with only some minor degradation seen in the Formulation D sample at the 4-week time point. No increase in degradation was seen in Formulation A.

TABLE 17

Assay and Related Substance Results for 4 week Short Term Stability Study for 200 mg Strength Tablets for Formulation D and Formulation A

| | Formulation D | | Formulation A | |
|---|---|---|---|---|
| Conditions/ Time Point | Assay % LC | Total Related Substance (%) | Assay % LC | Total Related Substance (%) |
| Initial | 99.1 | 0.74 | 100.5 | 0.73 |
| 40° C./75% RH Open 2 weeks | 100.0 | 0.63 | 102.4 | 0.55 |
| 40° C./75% RH Open 4 weeks | 99.9 | 0.70 | 100.7 | 0.73 |
| 50° C. Closed 2 weeks | 100.3 | 0.66 | 101.4 | 0.57 |
| 50° C. Closed 4 weeks | 97.4 | 1.00 | 100.0 | 0.72 |

From the experimentation performed, particularly the dissolution, it was observed that the Poloxamer 188 was a good surfactant and that croscarmellose sodium was a good disintegrant. High shear wet granulation proved to be an effective method of manufacture. The formulations using low shear wet granulation had less advantages in comparison with the formulations manufactured with the high shear wet granulation. The dissolution testing provided some such evidence of the differences between the two methods.

Example 8

Compression Studies Evaluating Formulation A and Formulation C

Tablet compression studies were performed on Formulation D, and Formulation A. Compression was performed on the Piccola BD Tablet Press at a speed of 36 rpm. Five main compression forces ranging from 3 to 10 kN was targeted to stress the formulation. Tablet weight (mg), tablet edge thickness, and tablet edge thickness (in) was measured.

The compression studies showed that all formulations were highly compressible. Formulation A started to reach its maximum hardness around 21 kp at 10.0 IN whereas Formulation D reached it maximum hardness around 16.3 kp at 9.9 kN. It was also seen in the compression studies that Formulation A required more force than Formulation D to achieve the same tablet thickness. Formulation D had slightly lower ejection forces. Formulation A provided higher hardness in comparison to Formulation D.

Example 9

Optimization of High Shear Granulation

The sieve analysis of the final blend of Formulation D indicated a high level of fines in the granulation (~50%). To further optimize formulation D, and reduce the level of fines in the granulation, experimentation was undertaken to possibly improve the high shear granulation process by increasing the amount of granulation fluid from 25% w/w (Formulation F) to 30% w/w (Formulation G). Formulations used in the optimization experimentation are presented in Table 18.

TABLE 18

Granulation Study of 200 mg Strength Formulations

| | Formulation G | | Formulation F | |
|---|---|---|---|---|
| INGREDIENT | Amount mg/tablet | Composition % by weight | Amount mg/tablet | Composition % by weight |
| Intragranular | | | | |
| Compound of Formula I | 200.0 | 57.1 | 200.0 | 57.1 |
| Microcrystalline Cellulose, NF Avicel PH 101 | 100.65 | 28.8 | 100.65 | 28.8 |
| Sodium Lauryl Sulfate, NF | — | — | — | — |
| Croscarmellose Sodium (Ac-Di-Sol) | 8.75 | 2.5 | 8.75 | 2.5 |
| Hydroxypropylcellulose, EXF | 10.5 | 3.0 | 10.5 | 3.0 |
| Poloxamer 188, NF | 17.5 | 5.0 | 17.5 | 5.0 |
| Sodium Starch Glycolate (EXPLOTAB ©) | — | — | — | — |
| Extragranular | | | | |
| Sodium Starch Glycolate (EXPLOTAB ©) | — | — | — | — |
| Croscarmellose Sodium (Ac-Di-Sol) | 8.75 | 2.5 | 8.75 | 2.5 |
| Colloidal Silicone Dioxide, NF (Cab-O-Sil M5P) | 0.35 | 0.1 | 0.35 | 0.1 |
| Magnesium Stearate, NF (Vegetable Grade) | 3.50 | 1.0 | 3.50 | 1.0 |
| Total | 350 | | 350 | |

Both batches of pre-granulation excipients were blended using a 1 Quart V Blender. The compound of formula I (API) was sandwiched between the blended excipients in the Niro PP-1 blended for 5 minutes with chopper off. The formulations were granulated by high shear granulation using the Niro PP1, equipped with a 7.5 liter insert. Milli-Q water was used as the granulation solution. The batch size was 1000 grams for Formulation G and 950 g for Formulation F due to limited API. Formulation G was granulated using 413 grams of water at a spray rate of 68.6 g/minute and Formulation F was granulated using 305 grams of water at a spray rate of 50.9 g/minute. The dried granulation was milled using a 197S Quadro Comil equipped with a 0.050" grater screen, a round impeller and a 0.175" spacer at 20% Comil speed. The extra-granular excipients were adjusted based on the percent yield of the final milled granulation.

The granulation was blended in a 2 quart V blender for 5 minutes after the addition of the croscarmellose and the colloidal silicon dioxide. The blend was blended an additional 3 minutes after the addition of the magnesium stearate. The blend was compressed on a Piccola BD Press using the paddle feed frame and hopper at a speed of 36 rpm. The 350 mg tablets were compressed with 0.2500"×0.5000" capsule standard concave tooling and the 700 mg tablets were compressed with 0.3300×0.7100 oval standard concave tooling.

The 200 mg strength tablets processed with 25% granulating fluid (Formulation F) were packaged 30 tablets per bottle in 50 cc HDPE bottles with induction sealed closures and placed on stability at 25° C./25% RH and 40° C./75% RH for up to 3 months along with the 200 mg strength Formulation A tablets.

The granulation of Formulation F had a finer, powdery appearance than Formulation G formed well defined granules. The fines were drastically reduced in Formulation G using 30% granulation fluid during processing as compared to Formulation F using 25% granulation fluid during processing in the sieve analysis of the final blends, and particle size distribution of the 30% granulation (Formulation G) was substantially larger than the 25% granulation (Formulation F) (Table 11). The final blends from both granulations were able to produce robust, good quality tablets with consistent, weight hardness and thickness and low friability (Table 12). Assay and related substance indicated no problem with potency or impurity. Disintegration time of the tablets roughly doubled with the increased 30% granulation from ~15 minutes to ~30 minutes (Table 14). Dissolution was also markedly slower with the 30% granulation tablets as compared to the 25% granulation tablets (Table 19).

TABLE 19

Dissolution of 200 mg Strength and 400 mg Strength Granulation Study Tablets Made with 25% versus 30% Granulation Fluid

| | % Dissolved vs Time (min) | | | | | | |
|---|---|---|---|---|---|---|---|
| Tablets Sample | 0 | 10 | 20 | 30 | 45 | 60 | 75 |
| Formulation F 200 mg strength tablets | 0 | 52 | 70 | 77 | 84 | 89 | 93 |
| Formulation G 200 mg strength tablets | 0 | 9 | 21 | 34 | 51 | 66 | 80 |
| Formulation F 400 mg strength tablets | 0 | 51 | 86 | 95 | 99 | 100 | 102 |
| Formulation G 400 mg strength tablets | 0 | 11 | 25 | 37 | 52 | 60 | 73 |

Example 10

Stability Study of Formulation F and A

Formulation F and Formulation A 200 mg strength tablets were packaged and placed on stability. The tablets were packaged 30 tablets per bottle in 50 cc HDPE bottles with induction sealed closures.

Both Formulation F and Formulation A were demonstrated to be stable for at least three months at 25° C./60% RH and 40° C./75% RH with regard to appearance, assay, related substances, dissolution, and moisture content. There was no indication of any instability (Table 20).

TABLE 20

Stability Data for Formulation F 200 mg Strength Tablets

| Conditions/Time point | TP# 25481 Appearance | TP# 64627 Assay % LC N = 2 | TP# 64627 Total Related Substance (%) | TP# 64512 Dissolution N = 6 | TP# 64730 % Water N = 2 |
|---|---|---|---|---|---|
| Initial | Conforms* | 100.0 | 0.61 | 30 min-91 60 min-98 | 1.6 |
| 25° C./60% RH 1 month | Conforms* | 100.5 | 0.53 | 30 min-92 60 min-95 | 1.5 |

TABLE 20-continued

Stability Data for Formulation F 200 mg Strength Tablets

| Conditions/<br>Time point | TP# 25481<br>Appearance | TP# 64627<br>Assay % LC<br>N = 2 | TP# 64627<br>Total Related<br>Substance (%) | TP# 64512<br>Dissolution<br>N = 6 | TP# 64730<br>% Water N = 2 |
|---|---|---|---|---|---|
| 25° C./60% RH<br>2 month | Conforms* | 101.8 | 0.61 | 30 min-89<br>60 min-97 | 2.1 |
| 25° C./60% RH<br>3 month | Conforms* | 100.1 | 0.53 | 30 min-87<br>60 min-95 | 2.1 |
| 40° C./75% RH<br>1 month | Conforms* | 100.3 | 0.59 | 30 min-88<br>60 min-93 | 1.5 |
| 40° C./75% RH<br>2 month | Conforms* | 100.1 | 0.61 | 30 min-89<br>60 min-94 | 2.1 |
| 40° C./75% RH<br>3 month | Conforms* | 99.8 | 0.71 | 30 min-89<br>60 min-95 | 2.1 |

*White to off-white, convex, oblong tablets with sides scored on one sides, contained in white HDPE bottle with foil seal (12.7 mm × 6.4 mm × 5.1 mm thick)

TABLE 21

Stability Data for Formulation A 200 mg Strength Tablets

| Conditions/<br>Time point | TP# 25481<br>Appearance | TP# 64627<br>Assay % LC<br>N = 2 | TP# 64627<br>Total Related<br>Substance<br>(%) | TP# 64512<br>Dissolution<br>N = 6 | TP# 64730<br>% Water<br>N = 2 |
|---|---|---|---|---|---|
| Initial | Conforms* | 100.5 | 0.73 | 30 min-90<br>60 min-96 | 2.1 |
| 25° C./60% RH<br>1 month | Conforms* | 101.6 | 0.67 | 30 min-87<br>60 min-96 | 2.2 |
| 25° C./60% RH<br>2 month | Conforms* | 101.7 | 0.80 | 30 min-88<br>60 min-95 | 2.9 |
| 25° C./60% RH<br>3 month | Conforms* | 101.0 | 0.73 | 30 min-86<br>60 min-94 | 2.4 |
| 40° C./75% RH<br>1 month | Conforms* | 102.7 | 0.62 | 30 min-84<br>60 min-97 | 2.2 |
| 40° C./75% RH<br>2 month | Conforms* | 101.0 | 0.72 | 30 min-87<br>60 min-93 | 3.0 |
| 40° C./75% RH<br>3 month | Conforms* | 100.4 | 0.69 | 30 min-87<br>60 min-93 | 2.6 |

*White to off-white, convex, oblong tablets with sides scored on one sides, contained in white HDPE bottle with foil seal (12.7 mm × 6.4 mm × 5.1 mm thick)

Example 11

Development of 100 mg Strength Formulation D Tablet and Evaluation of the Effect of API Particle Size The high shear granulation Formulation D was used to explore the dose proportional 100 mg strength tablet. The high shear granulation procedure utilizing the 25% granulation fluid was employed. In addition, the effect of utilizing a larger particle sized API (the compound of formula I) was evaluated by manufacturing 400 mg strength tablets as well as the 100 mg strength tablets from a common blend using a larger particle sized API to compare against previous batches of 400 mg strength tablets that used the smaller particle size API.

100 mg strength tablets were made using a high shear granulation procedure utilizing 25% granulation fluid with 57% drug load. Tablet weights of 175 mg were targeted to produce 100 mg strength tablets from Formulation D using API with larger particle size (Table 22).

TABLE 22

Composition of 100 mg Strength Tablets for Formulation D (Larger API Particle Size)

| Ingredient | Formulation D (larger API Particle Size) | |
|---|---|---|
| | Amount mg/tablet | Composition % by weight |
| Intragranular | | |
| API (Compound of formula I) | 100.0 | 57.1 |
| Microcrystalline Cellulose, NF Avicel PH 101 | 50.33 | 28.8 |
| Croscarmellose Sodium (Ac-Di-Sol) | 4.38 | 2.5 |
| Hydroxypropylcellulose, EXF | 5.25 | 3.0 |
| Poloxamer 188, NF | 8.75 | 5.0 |
| Extragranular | | |
| Croscarmellose Sodium (Ac-Di-Sol) | 4.38 | 2.5 |
| Colloidal Silicone Dioxide, NF (Cab-O-Sil M5P) | 0.175 | 0.1 |
| Magnesium Stearate, NF (Vegetable Grade) | 1.75 | 1.0 |
| Total | 175 | |

The assay value used to determine the adjusted weight of the compound of Formula I (API) was 98.80%. The total amount of compound of Formula I calculated for the batch was 578.4 grams for a 1 kg batch size. The excipients were bag blended and then used to sandwich the compound of Formula I into the PP-1 high shear granulator. The materials were charged to the PP-1 and premixed with impeller set on 306 rpm with no chopper for 3 minutes. Granulation was performed with the impeller speed set at 306 rpm with chopper speed on high. After the granulation evaluation, it was determined that additional water was needed. A total of 57.8 g of additional water was added to the granulation for a total water addition of 378.8 g at a rate of 53.5 g/min or 28% granulation fluid addition. The granulation was dried to an LOD of 0.7% in the MP-1 fluid bed with an inlet air temperature of 65° C. The granulation was milled using a 197S Quadro Comil equipped with a 0.050" grater screen using a 150 spacer at 20% speed. The resulting milled granulation yield was 80.1%. The extragranular excipients were adjusted and bag blended together. The resulting final blend was compressed using a gravity feed frame and hopper at approximated 42 rpm on a Korsch PHI 03 tablet press equipped with 0.2000×0.4000 oval plain (Hob#21971) tablet tooling for the 100 mg strength tablets and 0.3360× 0.6720 modified oval (Hob#1907) for the 400 mg strength tablets. A hardness of 10 kp and tablet weigh of 175 mg was targeted for the 100 mg strength tablets using Formulation D (larger API particle size) and a hardness of 15 kp and 700 mg weight was targeted for the 400 mg strength tablets using Formulation D (larger API particle size).

Evaluation of 100 mg and 400 mg Strength Tablets Using Formulation D (Larger API Particle Size)

The physical properties of the final blend were compared against previous batches of Formulation D (Table 13). The bulk density and flow properties as measured by compressibility and angle of repose were found to be very similar. Tap density of the final blend was found to be somewhat less than previous batches and the amount of fines in the sieve analysis was found to be substantially higher than in the previous formulation granulations utilizing 25% granulating fluid even though the granulation utilized 28% granulating fluid. The larger sized API appeared to affect the granulation properties. However, the final blend behaved well on the tablet press producing consistent tablets that met the tablet weight and hardness targets with low friability for both the 100 mg and 400 mg strength tablets. The tablet properties are presented in Table 13. Assay testing was performed on the 100 mg strength tablets and similar to all the previous formulations the potency was high (97.7%) the related substances were low (1.03% total). The dissolution testing on both the 100 mg and 400 mg strength tablets indicated a rapid rate of release that easily meets the criteria for an immediate release tablet. The dissolution profile is presented in Table 23.

TABLE 23

Dissolution of 100 mg and 400 mg Strength Tablets using Formulation D (Larger API Particle Size)

| Tablets Sample | % Dissolved vs Time (min) | | | | | | |
|---|---|---|---|---|---|---|---|
| | 0 | 10 | 20 | 30 | 45 | 60 | 75 |
| Formulation D (larger API particle size) 100 mg strength tablets | 0 | 45 | 83 | 90 | 93 | 94 | 95 |
| Formulation D (larger API particle size) 400 mg strength tablets | 0 | 55 | 83 | 90 | 92 | 93 | 94 |
| Formulation F 400 mg strength tablets | 0 | 51 | 86 | 95 | 99 | 100 | 102 |

Accordingly, the use of the larger particle sized API did not negatively affect the dissolution of the tablets or their manufacture. The dissolution profile of the Formulation D 400 mg strength tablets using the larger particle sized API was nearly identical to the stability batch Formulation F. However, the larger particle size did require the use of more granulation fluid in the manufacturing process.

Example 12

Utilizing the procedures described in examples 6 through 11, the tablets and capsules may contain the compound of formula I in amounts from about 10 mg to about 800 mg. The compound of formula I and inert ingredients are present in the described percentage amounts by weight, which are readily determined by one of ordinary skill in the art from the previous examples. For example, one of ordinary skill in the art, following the procedures of examples 1 through 12 in an analogous manner, can prepare tablets and capsules, in addition to those already set forth, wherein the compound of formula I is present in amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, or about 800 mg.

Example 13

The Phase IIa trial started with a 3-4 week placebo run-in period. 141 qualified stage I and II hypertensive patients were randomized to take either the compound of formula I 200 mg, 500 mg, or placebo, daily for 4 weeks. Key efficacy endpoints of mean 24 hour systolic ambulatory blood pressure monitoring (ABPM), mean 24 hour diastolic ABPM, mean seated office systolic blood pressure (SBP) and diastolic blood pressure (DBP), mean daytime SBP and DBP, mean nighttime SBP and DBP, and SBP and DBP during final 2 hours of dosing were assessed. 93 patients (efficacy population) were available for ABPM analysis.

The compound of formula I at either 200 mg or 500 mg once-daily produced a statistically significantly greater reduction in systolic and diastolic blood pressure in stage I and II hypertensive patients compared to placebo (Table 24). The drug was shown to be safe and well tolerated by patients. Most of the adverse events reported were mild or moderate in severity and included headaches and minor musculoskeletal and respiratory complaints (Table 25). There were no notable changes observed in liver function and hematology tests (Table 26).

TABLE 24

Efficacy Endpoints at Week 4 (End of Treatment)

| | Mean 24 hr ABPM Change (mmHg) | | Mean Seated Office Change (mmHg) | |
|---|---|---|---|---|
| | DBP | SBP | DBP | SBP |
| The compound of formula I 200 mg (n = 35) | −9.3[a] | −12.2[a] | −10.5[b] | −16.9[b] |
| The compound of formula I 500 mg (n = 33) | −10.1[a] | −14.8[a] | −9.8[b] | −17.3[b] |
| Placebo (n = 25) | +0.3 | −0.4 | +1.6 | −4.2 |

[a] $P < 0.001$ for each dose of the compound of formula I vs. placebo.
[b] $P < 0.001$ for each dose of the compound of formula I vs. placebo.

TABLE 25

Phase IIa Adverse Events (AE)

| | Placebo | The compound of formula I | |
|---|---|---|---|
| | N = 36 n (%) | 200 mg (N = 39) n (%) | 500 mg (N = 38) n (%) |
| At least one AE | 9 (25.0) | 8 (20.5) | 10 (26.3) |
| Musculoskeletal | 4 (11.1) | 1 (2.6) | 2 (5.3) |
| Peripheral Edema | 1 (2.8) | 0 | 1 (2.6) |
| Tachycardia | 1 (2.8) | 0 | 0 |
| Headache | 3 (8.3) | 2 (5.1) | 1 (2.6) |
| Confusion/anxiety/nervousness | 3 (8.3) | 0 | 0 |
| Respiratory | 2 (5.6) | 0 | 3 (7.9) |
| Nausea/gastritis | 1 (2.8) | 2 (5.1) | 1 (2.6) |
| Eczema | 0 | 1 (2.6) | 0 |

TABLE 26

Selected Laboratory Parameters

| | Placebo | The Compound of formula I | |
|---|---|---|---|
| | (N = 36) | 200 mg (N = 39) | 500 mg (N = 38) |
| Hematology | | | |
| Hb (g/dL) Mean Change from baseline | <+0.1 | −0.5 | −0.7 |
| Ht (%) Mean change from baseline | +0.3 | −1.7 | −2.2 |
| Liver Functions | | | |
| ALT (U/L) Mean change from baseline | +2.9 | −1.5 | −0.9 |
| AST (U/L) Mean change from baseline | +1.9 | −0.9 | −1.2 |
| γGT (U/L) Mean change from baseline | +3.4 | +0.3 | +0.8 |

Example 14

The Phase IIb trial started with a 4-week placebo run-in period and 261 qualified patients with SBP/DBP within 140-179/90-109 mmHg ranges were randomized to either the compound of formula I 200 mg, 400 mg, 800 mg, irbesartan 300 mg, or placebo, taken daily in the morning for 12 weeks. Key efficacy endpoints of seated SBP, DBP and % of patients with BP control (<140/90 mmHg), and all standard safety parameters were assessed. Results showed that each dose of the compound of formula I exhibited statistically dose-dependent greater BP decrease in SBP and DBP ($p<0.001$), and in BP control ($p<0.0013$) than placebo. Efficacy of the compound of formula I 200 mg was similar to irbesartan, 400 mg achieved better BP control than irbesartan ($p<0.05$) and 800 mg was statistically superior to irbesartan in all endpoints as demonstrated on Table 27. The onset of action of the compound of formula I was rapid within 4 hours and the efficacy was sustained over 12 weeks.

TABLE 27

Efficacy Endpoints at Week 12 (End of Treatment)

| | Mean SBP Change (mmHg) | Mean DBP Change (mmHg) | % Pts Achieving Goal (<140/90 mmHg) |
|---|---|---|---|
| The compound of formula I 200 mg (n = 58) | −13.2 | −7.2 | 36.2% |
| The compound of formula I 400 mg (n = 58) | −14.2 | −9.2 | 51.9%[b] |
| The compound of formula I 800 mg (n = 28) | −23.4[a] | −14.3[a] | 61.5%[a] |
| Irbesartan 300 mg (n = 58) | −10.7 | −7.1 | 31.5% |
| Placebo (n = 59) | 1.8[b] | 0.2[b] | 9.3%[c] |

[a] $P < 0.05$ vs. irbesartan.
[b] $P < 0.001$ for each dose of the compound of formula I vs. placebo.
[c] $P = 0.0013$ for the compound of formula I 200 mg vs. placebo; $P < 0.001$ for the compound of formula I 400 mg vs. placebo and 800 mg vs. placebo each.

No serious adverse events (SAEs) were reported during active treatment (Table 28). There were no notable changes observed in liver function tests (Table 29), creatinine, urea nitrogen and vital signs. In conclusion, the compound of formula I is a novel, dual mechanism of action, extremely potent agent that promises to be an important treatment of diabetic nephropathy, chronic or persistently elevated blood pressure, hypertension and other diseases.

TABLE 28

Phase IIb Most Frequent (≥5%) AEs During Treatment, n (%)

| Preferred Term/SOC Abbrev. | Placebo (n = 59) | The Compound of formula I | | | Irbesartan 300 mg (n = 58) |
|---|---|---|---|---|---|
| | | 200 mg (n = 58) | 400 mg (n = 58) | 800 mg (n = 28) | |
| Headache/Nerv | 10 (16.9) | 0 | 3 (5.2) | 2 (7.1) | 4 (6.9) |
| Odema peripheral/Genrl | 1 (1.7) | 2 (3.4) | 4 (6.9) | 3 (10.7) | 2 (3.4) |
| Dizziness/Nerv | 2 (3.4) | 0 | 2 (3.4) | 3 (10.7) | 2 (3.4) |
| Fatigue/Genrl | 1 (1.7) | 0 | 4 (6.9) | 0 | 3 (5.2) |
| Migraine/Gastr | 3 (5.1) | 0 | 2 (3.4) | 0 | 2 (3.4) |
| Diarrhea/Gastr | 0 | 1 (1.7) | 1 (1.7) | 2 (7.1) | 1 (1.7) |
| Abdominal pain/Gastr | 1 (1.7) | 1 (1.7) | 0 | 2 (7.1) | 0 |
| Urinary tract infection/Infec | 3 (5.1) | 0 | 0 | 1 (3.6) | 0 |

TABLE 29

| | Phase IIb: Liver Function Tests | | | |
|---|---|---|---|---|
| | Placebo | The Compound of formula I | | Irbesartan |
| | | 200 mg | 400 mg | 800 mg | 300 mg |
| ALT (U/L) Mean change from baseline | 2.4 | −0.4 | −3.2 | −7.3 | 0.2 |
| AST (U/L) Mean change from baseline | 1.7 | −1.2 | −1.5 | −5.4 | 0.1 |

Example 15

The study starts with qualified patients with diabetic nephrophathy. Screening assessments and evaluations may be conducted over a period of no more than 2 weeks. Following screening, all eligible patients will undergo a 4-week placebo run-in period to ensure that baseline blood pressure remains stable and continues to meet eligibility criteria for randomization. Eligible patients are randomized to instruct to either the compound of formula I: 200 mg, 400 mg, or 800 mg; irbesartan 300 mg; or placebo, taken daily for 12 weeks. Key efficacy endpoints of seated systolic BP, diastolic BP and % of patients with BP control (<140/90 mmHg), and all standard safety parameters are assessed. Changes from baseline to final measurement in the course of treatment are recorded.

It is expected that treatment by each dose of the compound of formula I of a human subject, for example a human subject having diabetic nephrophathy, will exhibits statistically dose-dependent greater BP decrease in SBP and DBP, and in BP control than placebo and irbesartan.

What is claimed is:

1. A method of treating glomerulosclerosis comprising administering to a subject in need thereof an effective amount of a compound of Formula I:

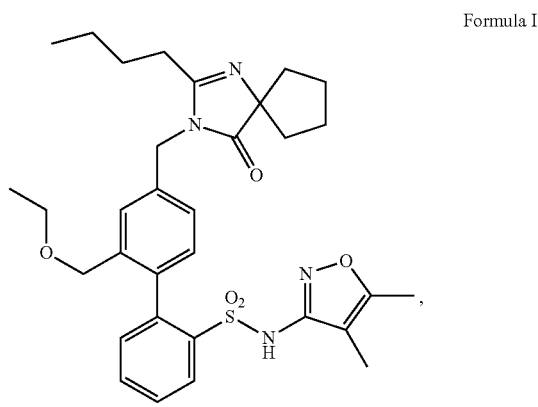 [SMILES: CCCCC1=NC2(CCCC2)C(=O)N1Cc1ccc(-c2ccccc2S(=O)(=O)Nc2noc(C)c2C)c(COCC)c1]

Formula I or a pharmaceutically acceptable salt thereof, wherein the amount of the compound of Formula I, or pharmaceutically acceptable salt thereof, administered to the subject is 200 mg/day, 400 mg/day, or 800 mg/day.

2. The method according to claim 1, wherein the amount of the compound of Formula I, or pharmaceutically acceptable salt thereof, administered to the subject is 200 mg/day.

3. The method according to claim 1, wherein the amount of the compound of Formula I, or pharmaceutically acceptable salt thereof, administered to the subject is 400 mg/day.

4. The method according to claim 1, wherein the amount of the compound of Formula I, or pharmaceutically acceptable salt, administered to the subject is 800 mg/day.

* * * * *